(12) United States Patent
Eckert et al.

(10) Patent No.: US 7,799,846 B2
(45) Date of Patent: Sep. 21, 2010

(54) DENTAL COMPOSITION CONTAINING AN EPOXY FUNCTIONAL CARBOSILANE COMPOUND

(75) Inventors: Adrian S. Eckert, Munich (DE); Peter Bissinger, Diessen (DE); Karsten Dede, Landsberg (DE); Thomas Klettke, Diessen (DE)

(73) Assignee: 3M ESPE AG, Seefeld (DE)

( * ) Notice: Subject to any disclaimer, the term of this patent is extended or adjusted under 35 U.S.C. 154(b) by 828 days.

(21) Appl. No.: 11/572,062

(22) PCT Filed: Jul. 14, 2004

(86) PCT No.: PCT/EP2004/007791

§ 371 (c)(1),
(2), (4) Date: Jan. 12, 2007

(87) PCT Pub. No.: WO2006/005369

PCT Pub. Date: Jan. 19, 2006

(65) Prior Publication Data

US 2008/0031830 A1  Feb. 7, 2008

(51) Int. Cl.
*A61K 6/093* (2006.01)
*A61C 5/00* (2006.01)
*A61C 5/08* (2006.01)
*C08G 77/60* (2006.01)

(52) U.S. Cl. .................. 523/116; 528/42; 528/43; 433/218; 433/228.1

(58) Field of Classification Search ............. 523/116; 528/42, 43; 433/228.1
See application file for complete search history.

(56) References Cited

U.S. PATENT DOCUMENTS

| 3,971,754 | A | 7/1976 | Jurecic |
| 4,391,590 | A | 7/1983 | Dougherty |
| 4,767,798 | A | 8/1988 | Gasser et al. |
| 4,788,268 | A | 11/1988 | Lau et al. |
| 5,165,890 | A | 11/1992 | Discko |
| 5,322,440 | A | 6/1994 | Steele |
| 6,084,004 | A | 7/2000 | Weinmann et al. |
| 6,387,981 | B1 | 5/2002 | Zhang |
| 6,572,693 | B1 | 6/2003 | Wu et al. |
| 6,779,656 | B2 * | 8/2004 | Klettke et al. ............ 206/219 |
| 2005/0252413 | A1 | 11/2005 | Kangas et al. |
| 2005/0252414 | A1 | 11/2005 | Craig et al. |
| 2005/0256223 | A1 | 11/2005 | Kolb et al. |

FOREIGN PATENT DOCUMENTS

| EP | 0 238 025 A1 | 9/1987 |
| EP | 0 897 710 A2 | 2/1999 |
| WO | WO 98/22521 | 5/1998 |
| WO | WO 98/47046 | 10/1998 |
| WO | WO 98/47047 | 10/1998 |
| WO | WO 00/19967 | 4/2000 |
| WO | WO 01/30305 | 5/2001 |
| WO | WO 01/30306 | 5/2001 |
| WO | WO 01/30307 | 5/2001 |
| WO | WO 01/51540 A2 | 7/2001 |
| WO | WO 02/066535 A1 | 8/2002 |
| WO | WO 03/063804 A1 | 8/2003 |

OTHER PUBLICATIONS

Marciniec, B., Comprehensive Handbook on Hydrosilylation, Pergamon Press, Oxford, 1992.
Beck, H., N., Chaffee, R., G., J. chem. Eng. Data 1963, 8(3), 453-454.
Houben-Weyl, Methoden d. Organ. Chemie, vol. VI/3, p. 385ff., Georg Thieme Verlag, Stuttgart, 1965, 4. edition.
DIN EN ISO 4049, 2001.
DIN EN ISO 9917-1, 2004.
DIN EN ISO 9917-2, 1999.

* cited by examiner

*Primary Examiner*—Tae H Yoon
(74) *Attorney, Agent, or Firm*—Pamela L. Stewart

(57) ABSTRACT

The present invention relates to a dental composition comprising least one carbosilane compound comprising at least one Si-Aryl bond, at least one silicon atom, no Si-Oxygen bond, at least one aliphatic epoxy moiety, wherein said carbosilane compound has no glycidyl ether moieties; and an initiator, optionally filler and optionally additive components selected from the group of modifiers, stabilizers, dyes, pigments, thixotropic agents, flow improvers, polymeric thickeners, surfactants, odorous substances, diluting agent(s) and flavorings.

21 Claims, No Drawings

US 7,799,846 B2

DENTAL COMPOSITION CONTAINING AN EPOXY FUNCTIONAL CARBOSILANE COMPOUND

CROSS REFERENCE TO RELATED APPLICATIONS

This application is a national stage filing under 35 U.S.C. 371 of PCT/EP2004/007791 filed Jul. 14, 2004.

The present invention relates to a curable dental composition containing an epoxy functional carbosilane compound. The composition has improved properties and can be used e.g. as a dental filling material.

BACKGROUND

Composites are well known dental restorative materials on the market. However most of the organic based dental restoratives to date are based on methacrylate and/or acrylate chemistry. The newer materials based on oxirane chemistry presume lower polymerization shrinkage and lower stress.

WO 98/47046 describes a photocurable, addition polymerizable composition which contains an epoxy resin and a photoinitiator system. The epoxy resin include glycidyl ether monomers.

WO 00/19967 discloses a dental composition useful for making dental prostheses or dental restorations comprising a silicone oligomer or polymer. The compositions possess epoxy-reactive groups and are polymerizable via a cationic cure process.

WO 98/22521 describes polymerizable substances containing an epoxide or a mixture of epoxides, a filler material, initiators, inhibitors and/or accelerators. The substances include cycloaliphatic epoxy functions with a relatively high viscosity.

WO 01/51540 discloses polymerizable compositions based on epoxies that contain silicon. The compositions are based on silane compounds with cycloaliphatic epoxy functional groups. These cycloaliphatic epoxy-functional group-containing compounds have a relatively high viscosity. This leads on the one hand to inferior handling properties and to poor mechanical properties because a reduced amount of filler must be used to prepare the dental compositions.

A disadvantage of the dental composites on the market is that the epoxy-functional polymerizable resins do not possess refractive indices similar to these of the fillers commonly used to prepare dental composites. This results in an increased opacity of the composite which leads to poor esthetic properties in the cured material. A further drawback of some of the epoxy-functional dental composite materials on the market is that they contain components that are not hydrolytically very stable and can decompose in the mouth over the years releasing undesirable substances.

It is thus an object of the present invention to alleviate one or more of the problems mentioned above.

It is another object of the present invention to provide a composition with improved properties, especially to provide an esthetic composition for use in the dental field.

It is a further object of the present invention to provide a composition wherein the refractive index of the curable resin is similar to the refractive index of the used fillers.

SUMMARY OF THE INVENTION

The terms "comprise" and "contain" within the meaning of the invention introduce a non exhaustive list of features. Likewise, the word "one" or "a" is to be understood in the sense of "at least one".

The term "dental composition" according to the invention is a curable composition to be used in the dental field for different purposes, usually in small amounts of a few grams.

It has been found that one or more of the above mentioned objects can be achieved by providing a composition as described in the text below.

Surprisingly, it has been found that using carbosilane compounds comprising polymerizable groups such as aliphatic epoxies that do not contain carbosiloxane or glycidyl ether groups enables one to provide curable dental compositions with improved properties.

Thus, the present invention relates to a curable dental composition comprising a) at least one carbosilane compound comprising
   at least one Si-Aryl bond,
   at least one silicon atom,
   no Si-Oxygen bond,
   at least one aliphatic epoxy moiety;
wherein said carbosilane compound has no glycidyl ether moieties; and
b) initiator,
c) optionally filler,
d) optionally additive components selected from the group of modifiers, stabilizers, dyes, pigments, thixotropic agents, flow improvers, polymeric thickeners, surfactants, odorous substances, diluting agent(s) and flavorings.

The Aryl of the mandatory Si-Aryl bond of the carbosilane compound is an aromatic moiety comprising preferably six to 20 carbon atoms. It can be substituted by any atom or any moiety that does not interfere with the function of the invention. Examples for the aromatic moiety are substituted or non substituted groups selected from phenyl, naphthyl, alkoxyphenyl, alkoxy naphthyl, bisphenol A ethers and/or bisphenol F ethers.

One or more carbosilane compounds can be used alone or in a mixture with other components comprising aliphatic epoxy and/or cycloaliphatic epoxy functionalities and/or polymerizable compounds of other functionalities than epoxy as reactive compounds to prepare dental materials within the scope of the invention. Compositions of the invention may also contain other reactive and/or unreactive components if desired.

The present invention also relates to a method of producing the dental composition as described below.

Additionally, the present invention relates to a method of using the composition as described below.

The carbosilane compounds of the invention show high refractive indices together with low viscosity. The high refractive index is similar to the refractive indices of commonly used fillers. Therefore, dental compositions showing an excellent opacity and high esthetic properties can be achieved by using the carbosilane compound of the invention.

Another advantage of the dental compositions described by the invention is their appropriate lipophilicity.

Moreover, the compositions show comparably low shrinkage as well as low uptake of water and/or water soluble dyes (e.g. from coffee, tea, red wine) after curing compared to other dental compositions on the market.

Surprisingly it was found that the carbosilane compound of the present invention could co-polymerize with cycloaliphatic epoxy compounds. This was not expected as it is known from the art that common epoxies, e.g. glycidyl ether containing aliphatic epoxies, do not properly co-polymerize with cycloaliphatic epoxy compounds.

The carbosilane compounds preferably have a refractive index from 1.500 to 1.600, more preferably from 1.510 to 1.580, and most preferably from 1.520 to 1.560.

The viscosities of the carbosilane compounds are preferably from 0.01 to 40 Pas, more preferably from 0.1 to 20 Pas, and most preferably from 1 to 5 Pas.

The carbosilane compounds preferably have an average molecular mass of 300 to 10 000 g/mol, preferably from 800 to 10 000 g/mol, and more preferably from 1200 to 5000 g/mol.

The dental composition of the invention preferably comprises from 1 to 90 wt.-%, preferably from 3 to 65 wt.-%, and more preferably from 10 to 30 wt.-% of one or more carbosilane compounds.

The amount of initiator is preferably from 0.01 to 25 wt.-%, more preferably from 0.5 to 10 wt.-%, and most preferably from 0.5 to 3 wt.-% of the curable composition.

If filler is present in the dental composition, it is preferably present in an amount of 0 to 90 wt.-%, more preferably from 25 to 80 wt.-% and most preferably from 50 to 75 wt.-%.

If one or more of the additive components is present in the curable composition, they are preferably present at a total amount from 0 of 25 wt.-%, preferably from 0 to 15 wt.-%, more preferably from 0 to 3 wt.-%., depending on the application of the curable dental composition.

All of these above mentioned ranges are calculated as wt.-% of the curable composition.

Preferably, the curable dental composition of the invention possesses at least one of the following characteristics when in the cured state:

The opacity of the cured dental composition, preferably is from 10 to 93%. More preferably it is from 40 to 91% and most preferably it is from 70 to 89%.

The compressive strength of the cured dental composition is preferably greater than about 150 MPa, more preferably greater than about 200 MPa, and most preferably greater than about 250 MPa.

The flexural strength of the cured dental composition is preferably greater than 50 MPa, more preferably greater than 65 MPa, and most preferably greater than 80 MPa.

The carbosilane compound of the inventive composition comprises:
- at least one, preferably two, more preferably two to four Si-Aryl bonds,
- at least one, preferably two to six, more preferably two to four silicon atoms,
- at least one, preferably two to six, more preferably two to four aliphatic epoxy moieties,
- no Si-Oxygen bond,
- at least one, preferably at least two, more preferably at least four aromatic moieties,
- optionally a bisphenol derived spacer moiety, wherein said carbosilane compound has no glycidyl ether moieties.

In one embodiment of the invention the dental composition comprises one or a mixture of different carbosilane compounds which comprise at least one group of the following general formula (A'):

Aryl-[Si(A)$_a$(D-B)$_b$]$_n$     (A')

wherein each A independently represents an aliphatic or cycloaliphatic moiety having one to six carbon atoms (preferably one carbon atom), an aromatic moiety having six to 14 carbon atoms (preferably phenyl) or an aliphatic aromatic or aromatic aliphatic moiety having 8 to 16 carbon atoms (preferably 8 carbon atoms, e.g. 2-phenylethyl), each B independently represents an aliphatic epoxy moiety having two to six carbon atoms, preferably a terminal $C_2$ based epoxy moiety, each D independently represents an aliphatic or cycloaliphatic moiety having two to 10 carbon atoms (preferably four to 8 carbon atoms), an aromatic or aromatic aliphatic moiety having six to 14 carbon atoms, wherein one or more C or H atoms can be replaced by O, Br, Cl or Si, each Aryl independently represents a substituted or non substituted aromatic moiety having six to 14 carbon atoms, a is 0, 1 or 2, preferably is 2;

b is 1, 2 or 3, preferably is 1;

a+b=3 n is 1, 2, 3, 4, 5 or 6, preferably is 2, and wherein the carbosilane compound does not contain a glycidyl ether moiety.

Preferred for some embodiments of the invention is a substituent D having seven carbon atoms, e.g. α,3- or α,4-toluenediyl with the phenyl ring attached to Si and the methylene group attached to aliphatic epoxy moiety B.

Aryl represents an substituted or non substituted aromatic moiety. The aromatic moiety comprises six to 14 carbon atoms. Said substituents of the aromatic moiety having one to 10 carbon atoms can be branched or unbranched and one or more C or H atoms can be replaced by O, Br, Cl or Si.

Besides at least one attached Si-Atom according to general formula (A'), the aromatic moiety (Aryl) may be substituted preferably by one or two substituents as mentioned above, preferably alkyl, aryl, alkyl ether and/or aryl ether groups having one to 10 carbon atoms (e.g. $C_{1-8}$ alkyl, $C_{2-10}$ alkenyl, $C_{3-6}$ cycloalkyl, $C_{4-6}$ cycloalkenyl, $C_{6-10}$ aryl) and/or (2,3-epoxypropyl) groups.

Examples for Aryl are benzene, (2,3-epoxypropyl)benzene, naphthalene, alkoxybenzenes, alkoxy naphthalenes, bisphenol A ethers and/or bisphenol F ethers.

The epoxy functional moiety B is attached onto a spacer D. This spacer D can be a mixture of different types of spacers of similar and/or non similar chemical structure within the same molecule. The use of a mixture of different types of spacers D within the same molecule is of special interest concerning to the tailor-made adjustment of viscosity and/or reactivity and/or polarity and/or refractive index of the carbosilane compound as well as of the properties of the cured dental composition like stiffness.

The carbosilane compound of the inventive composition has a comparably high refractive index together with a comparably low viscosity. The carbosilane compound further shows a comparably high lipophilicity and a comparably high molecular weight.

A high refractive index and a high lipophilicity are of interest for dental materials to achieve appropriate esthetics as well as to avoid staining and/or swelling by uptake of water and/or water soluble dyes (e.g. from coffee, tea, red wine).

Depending among others on the chemical structure of the spacer D or the chemical structures of a mixture of different types of spacers D a comparably low viscosity of carbosilane compound can be adjusted which might be of some importance for dental materials to achieve appropriate handling properties.

In preferred embodiments the carbosilane compound can be characterized by one of the following formulas (I-IV)

depending on the molecular structure of the carbosilane compound as well as on the number m of the structural elements $\{Aryl-[Si(A)_a(D-B)_b]_n\}_m$ within the carbosilane compound.

In a preferred embodiment the carbosilane compound comprises only one structural element $\{Aryl-[Si(A)_a(D-B)_b]_n\}_m$ (i.e. m=1) as well as only one Aryl-Si bond (i.e. n=1) which can be characterized by formula (Ia):

$$\{Aryl-[Si(A)_a(D-B)_b]_n\}_m \quad (Ia)$$

wherein m is 1 n is 1

According to formula (Ia) the following compounds are preferred examples of carbosilane compound:

wherein

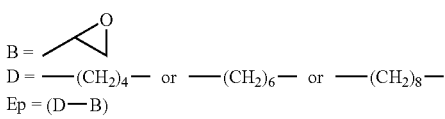

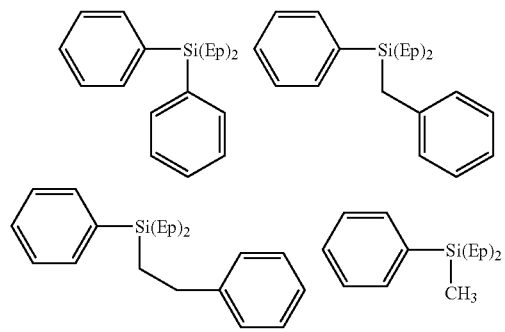

In another preferred embodiment the carbosilane compound comprises only one structural element $\{Aryl-[Si(A)_a(D-B)_b]_n\}_m$ (i.e. m=1) as well as only one Aryl-Si bond (i.e. n=1) which can be characterized by formula (Ib):

$$B-D-E-\{Aryl-[Si(A)_a(D-B)_b]_n\}_m \quad (Ib)$$

wherein m is 1 n is 1

E represents an aliphatic or cycloaliphatic moiety having five to 11 carbon atoms, preferably seven to 9 carbon atoms, wherein one or more C or H atoms can be replaced by O, Br, Cl or Si, and wherein the other indices are as defined above.

It is further preferred that E represents an aliphatic or cycloaliphatic moiety having five to 11, preferably seven to 9 carbon atoms wherein at least one C atom must be replaced by a Si atom and wherein one or more C or H atoms can be replaced by O, Br, Cl or Si.

According to formula (Ib) the following compounds are preferred examples of carbosilane compound:

wherein

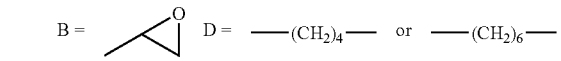
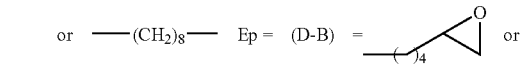

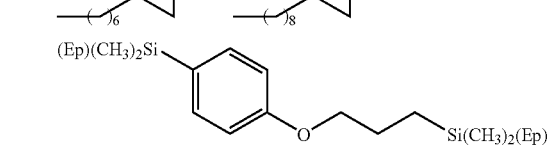

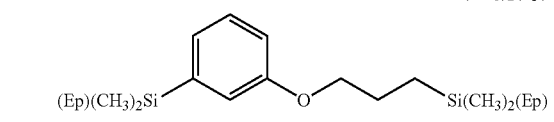

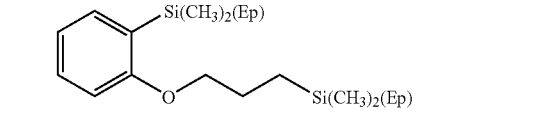

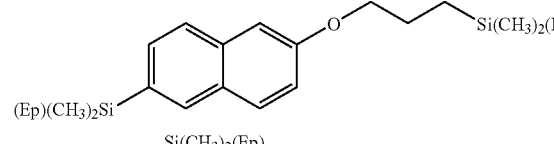

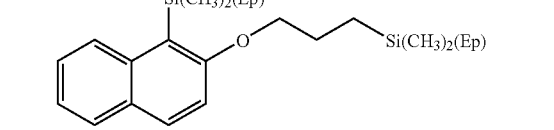

In a further embodiment the carbosilane compound comprises only one structural element $\{Aryl-[Si(A)_a(D-B)_b]_n\}_m$ (i.e. m=1) as well as more than one Aryl-Si bond (i.e. n≧2). It can be characterized by formula (II):

$$\{Aryl-[Si(A)_a(D-B)_b]_n\}_m \quad (II)$$

wherein m is 1, n is 2, 3, 4, 5 or 6, preferably is 2 or 3, wherein the other indices are as defined above.

According to formula (II) the following examples are preferred carbosilane compound:

wherein

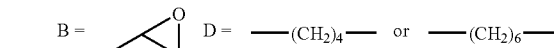
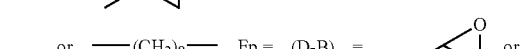
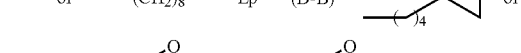

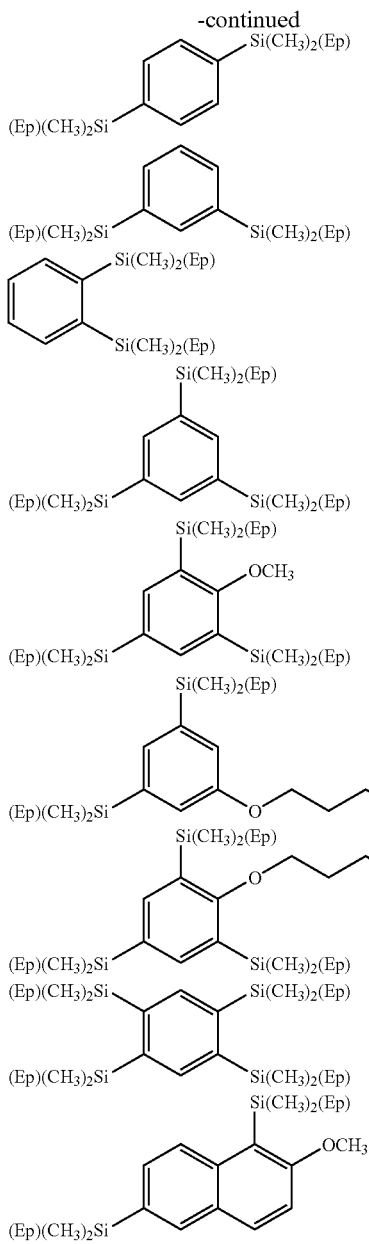
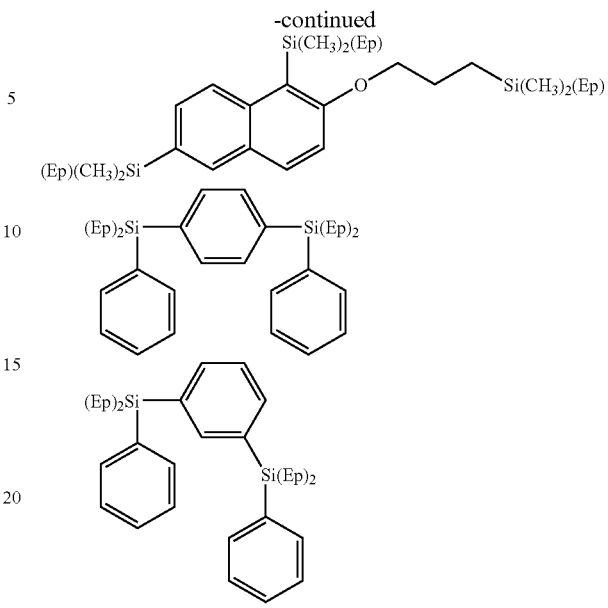

In a further preferred embodiment the carbosilane compound comprises at least one structural element {Aryl-[Si(A)$_a$(D-B)$_b$]$_n$}$_m$ as well as more than one Aryl-Si bond (i.e. the aromatic moieties are always attached to a silicon atom) which can be characterized by formulas (IIIa and IIIb) depending on m (i.e. m≧2 or m=1):

$$F\text{-}\{Aryl\text{-}[Si(A)_a(D\text{-}B)_b]_n\}_m \quad \text{(IIIa)}$$

wherein m is 2, 3 or 4, preferably is 2, n is 1, 2, 3, 4, 5 or 6, preferably is 2, F represents an aliphatic or cycloaliphatic moiety having 0 to 25 carbon atoms (preferably 0 to 9 carbon atoms) or an aromatic moiety having 0 to 20 carbon atoms (preferably six to 10 carbon atoms) wherein one or more C or H atoms can be replaced by O, Br, Cl or Si, and wherein the other indices are as defined above.

Preferred examples of carbosilane compound according to formula (IIIa) are given below:

wherein

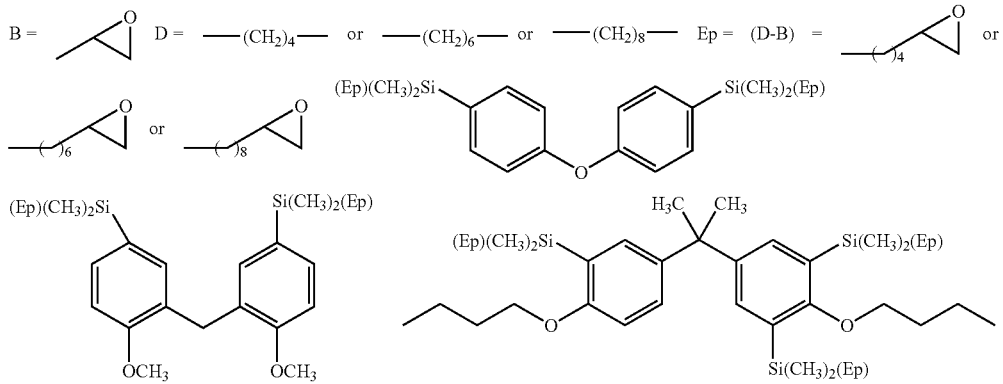

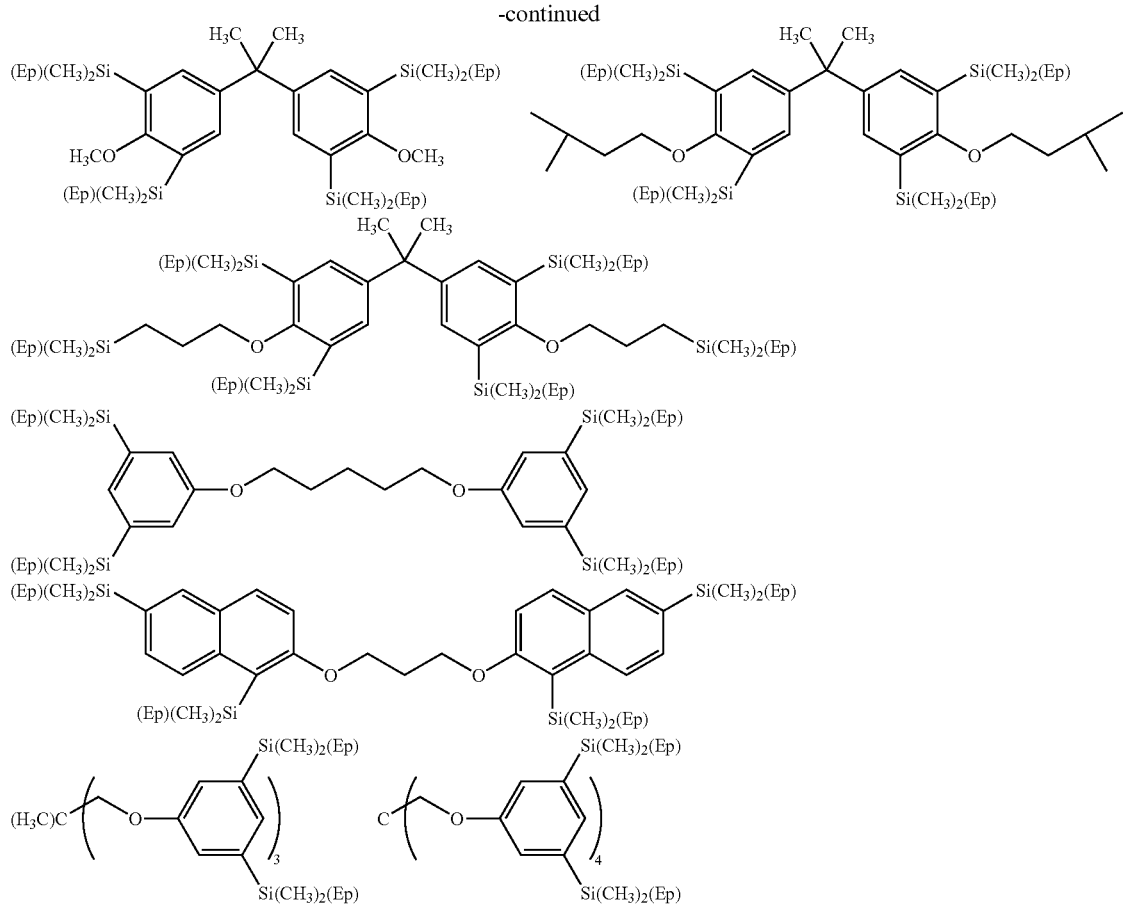

In a preferred embodiment the carbosilane compound comprises only one silicon atom and more than one aromatic moiety each attached to the silicon atom within the molecule in the structural element Aryl-[Si(A)$_a$(D-B)$_b$]$_n$ (i.e. n=1, b≧1) which can be characterized by formula (IIIb), wherein the indices are as defined above:

Aryl-[Si(A)$_a$(D-B)$_b$]$_n$     formula (IIIb)

wherein

Aryl represents (2,3-epoxypropyl)benzene, each A independently represents an aliphatic or cycloaliphatic moiety having one to six carbon atoms (preferably C$_1$) or an aromatic or aliphatic aromatic moiety having six to 16 carbon atoms (preferably 8 carbon atoms, e.g. (2-phenylethyl)), each B independently represents a terminal C$_2$ based epoxy moiety, each D independently represents an aromatic aliphatic moiety having seven to 14 carbon atoms, preferably α,3- or α,4-toluenediyl with the phenyl ring attached to Si and the methylene group attached to aliphatic epoxy moiety B, a is 0, 1 or 2 b is 1, 2 or 3 n is 1 wherein the other indices are as defined above.

Preferred examples of carbosilane compound according to formula (IIIb) are as follows wherein

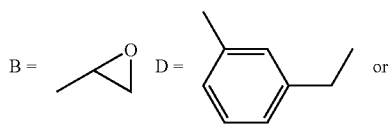

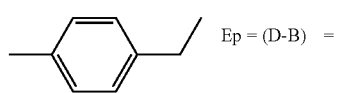

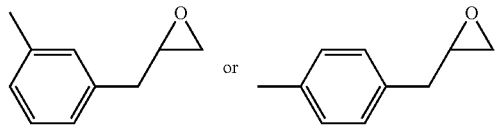

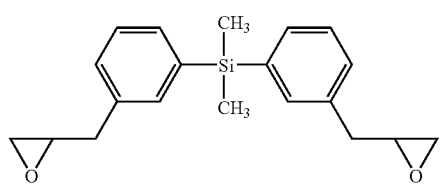

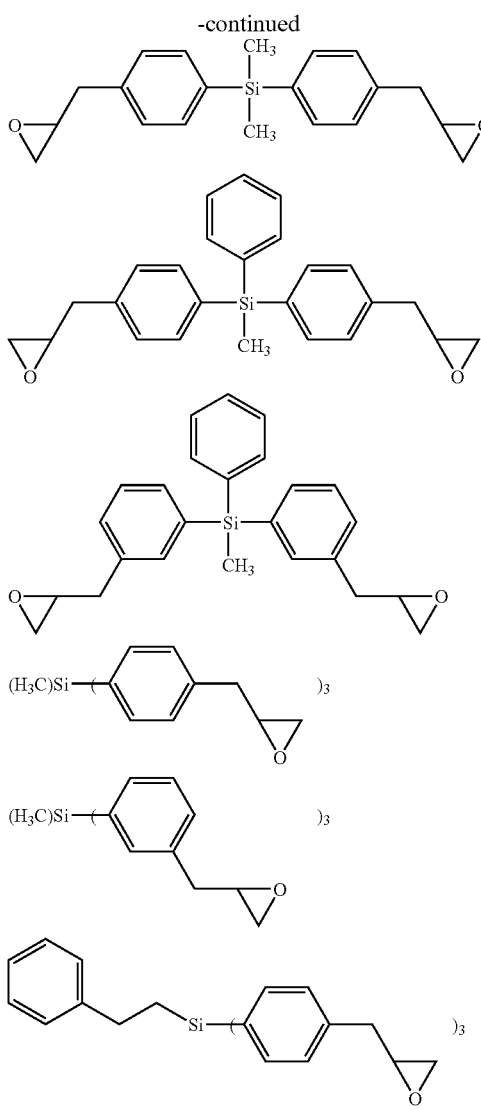

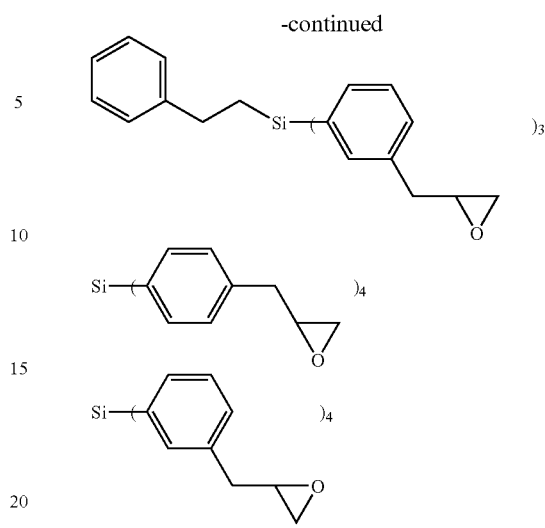

In a preferred embodiment the carbosilane compound comprises more than one aromatic moiety within the molecule not only in the structural element $\{Aryl\text{-}[Si(A)_a(D\text{-}B)_b]_n\}_m$ (i.e. the aromatic moieties are not always attached to silicon atoms) which can be characterized by formula (IV):

$$G\text{-}\{Aryl\text{-}[Si(A)_a(D\text{-}B)_b]_n\}_m \qquad (IV)$$

wherein

G represents an aliphatic, cycloaliphatic, aromatic, (cyclo)aliphatic aromatic or aromatic (cyclo)aliphatic moiety having one to 200 carbon atoms (preferably three to 63 carbon atoms) wherein one or more C or H atoms can be replaced by O, Br, Cl, and Si, m is 2, 3 or 4, preferably is 2 n is 1, 2, 3, 4, 5 or 6, preferably is 2, wherein the other indices are as defined above.

Preferred examples of carbosilane compound according to formula (IV) are as follows wherein

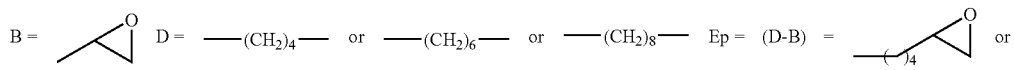

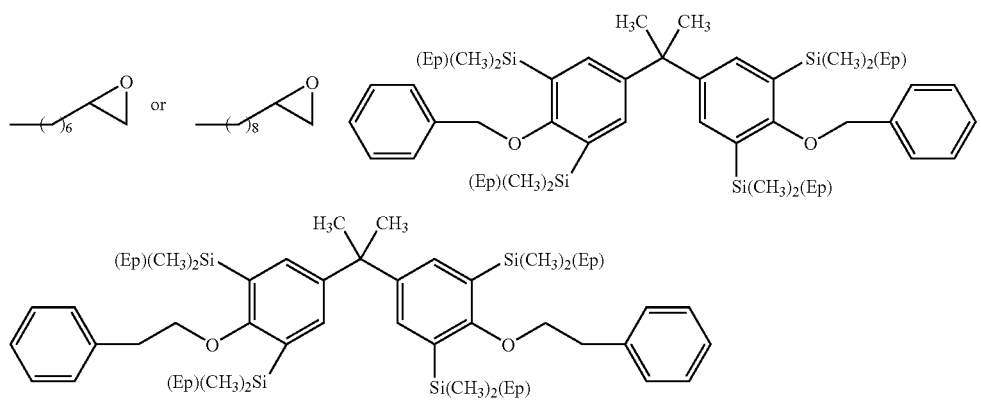

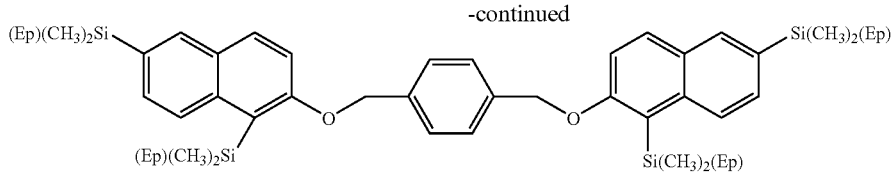
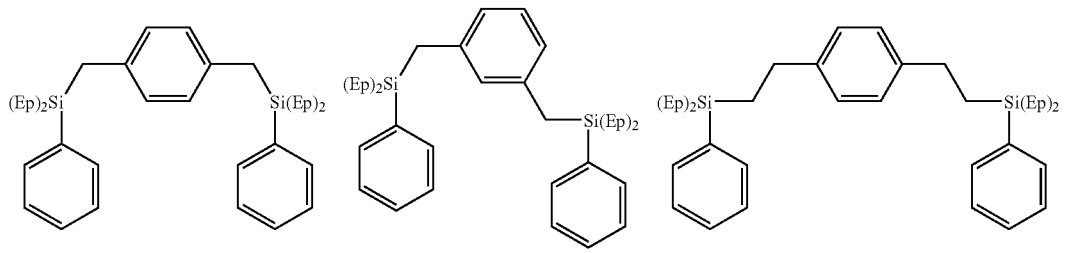
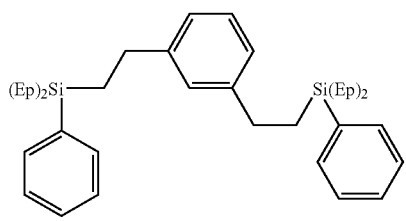
In a more detailed embodiment of formula (IV) with m=2, the carbosilane compound according to formula (IV) can be represented by formula (IVa)
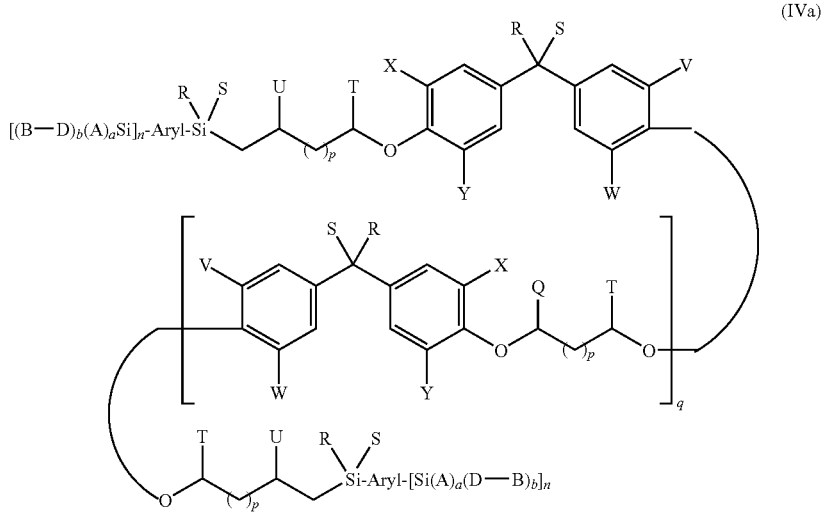

wherein each Q independently represents H or methyl, each R, S independently represent H, phenyl or a branched or unbranched alkyl moiety having one to 8 carbon atoms, wherein R and S together may form a cycloaliphatic ring each T, U independently represent H, methyl or ethyl, each V, W, X, Y independently represent H, Br, Cl or F, p is 0, 1, 2, 3 or 4 q is 0, 1, 2, 3, 4 or 5, wherein the other indices are as defined above.

Preferred examples of carbosilane compound according to formula (IVa) are as follows wherein

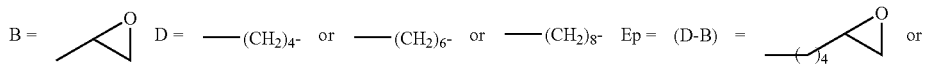

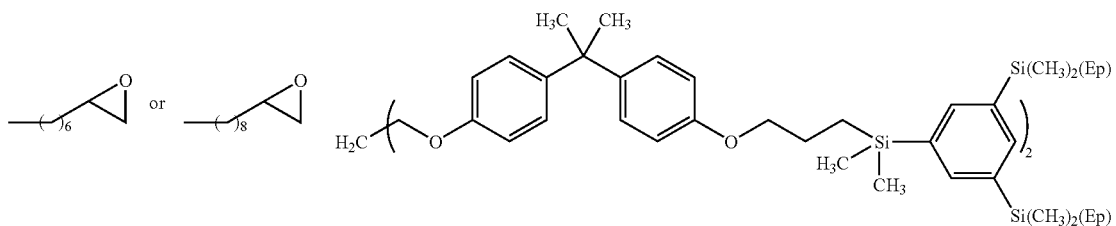

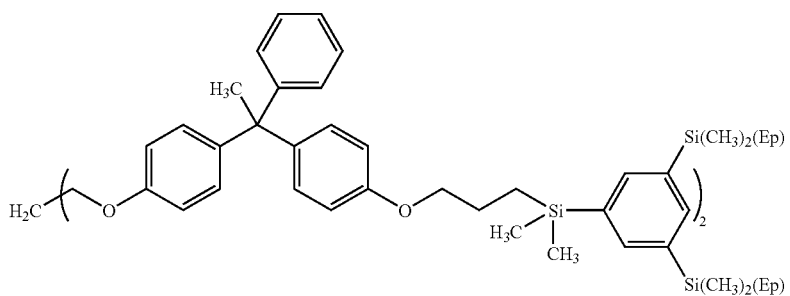

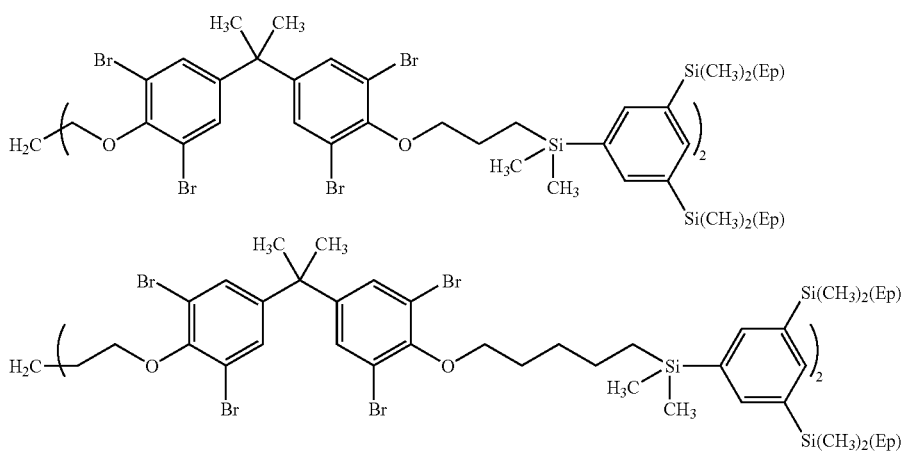

In another more detailed embodiment of formula (IV) with m=2, for q=0 the carbosilane compound according to formula (IV) can be represented by formula (IVb),
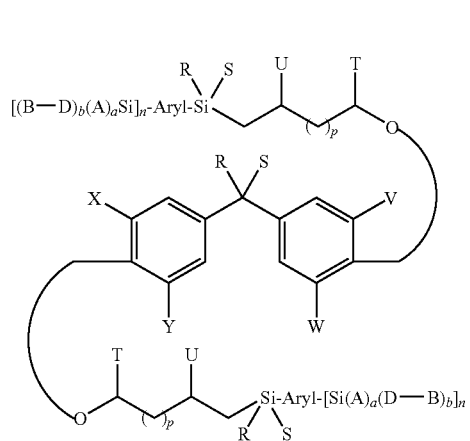
(IVb)
wherein the indices are as defined above.
Preferred examples of carbosilane compound according to formula (IVb) are as follows
wherein
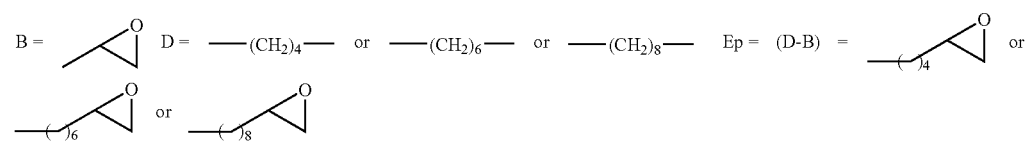

Useful initiators can initiate curing of carbosilane compound of the composition. Such initiators can be light curing or chemical curing or redox curing. All types of initiators are well known to the skilled person in the art.

Examples of such initiators are for example Lewis or Broensted acids, or compounds which liberate such acids, which initiate the polymerization, for example $BF_3$ or ether adducts thereof ($BF_3$.THF, $BF_3$*$Et_2O$, etc.), $AlCl_3$, $FeCl_3$, $HPF_6$, $HAsF_6$, $HSbF_6$ or $HBF_4$, or substances which initiate the polymerization after irradiation by UV or visible light or by means of heat and/or pressure, such as e.g. (eta-6-cumene)(eta-5-cyclopentadienyl)iron hexafluorophosphate, (eta-6-cumene) (eta-5-cyclopentadienyl)iron tetrafluoroborate, (eta-6-cumene)(eta-5-cyclopentadienyl)iron hexafluoroantimonate, substituted diaryliodonium salts and triarylsulphonium salts. Accelerators which can be employed are peroxy compounds of the perester, diacyl peroxide, peroxydicarbonate and hydroperoxide type. Hydroperoxides are preferably used, and cumene hydroperoxide in an approximately 70 to 90% solution in cumene is employed as the particularly preferred accelerator. The ratio of photoinitiator to cumene hydroperoxide can be varied within wide limits from 1:0.001 to 1:10, but the ratio used is preferably 1:0.1 to 1:6, and particularly preferably 1:0.5 to 1:4. The use of complexing agents, such as, for example, oxalic acid, 8-hydroxyquinoline, ethylenediaminetetraacetic acid and aromatic polyhydroxy compounds, is possible.

Likewise initiator systems consisting of different components can be used as described in EP 0 897 710 A1, WO 98/47046 or WO 98/47047. Systems comprising 1,2-diketones (as e.g. Camphorquinone), iodoniumium salts with poor coordinating anions (as e.g. Tolylcumyliodonium tetrakis(pentafluorophenyl)borate or Tolylcumyliodonium tetrakis(3,5-bis(trifluoromethyl)-phenyl)borate) together with tertiary aromatic amines (as e.g. benzoates like 2-butoxyethyl 4-(dimethylamino)benzoate, ethyl 4-(dimethylamino)benzoate) and/or suitable polycondensed aromatic compounds (as e.g. anthracene) are used as preferred initiator systems.

The composition of the present invention may also include one or more fillers which might be dental fillers. Preferably used are inorganic fillers like quartz, ground glasses, silica gels as well as pyrogenic silicic acids and precipitation silicic acids or their granules. X-ray-opaque fillers are also preferably used, at least partially. These can be, for example, X-ray-opaque glasses, such as glasses which contain strontium, barium or lanthanum (e.g. those described in U.S. Pat. No. 3,971,754). Some of the fillers may consist of an X-ray-opaque additive, such as for example yttrium trifluoride, strontium hexafluorozirconate or fluorides of the rare earth metals (e.g. according to EP 0 238 025 A1). For better incorporation into the polymer matrix, it is advantageous to hydrophobize the inorganic fillers. Customary hydrophobization agents are silanes, e.g. (3-Glycidyloxypropyl)trimethoxysilane or [2-(3,4-Epoxycyclohexyl)-ethyl]trimethoxysilane. The fillers preferably have an average grain size <20 µm, preferably <5 µm and in particular <2 µm and an upper grain limit of 150 µm, preferably 70 µm and in particular 25 µm. Such fillers can be present in amounts of from about 3 to about 90 weight percent, especially from about 25 to about 80 wt.-% or from about 50 to about 75 wt.-% of the composition.

Other suitable fillers are disclosed in U.S. Pat. No. 6,387,981 and U.S. Pat. No. 6,572,693 as well as in WO 01/30305, WO 01/30306, WO 01/30307 and WO 03/063804. Filler components described in these references include nanosized silica particles, nanosized metal oxide particles, and combinations thereof. Nanofillers are also described in U.S. patent applications entitled, "Dental Compositions Containing Nanozirconia Fillers," 10/847,782; "Dental Compositions Containing Nanofillers and Related Methods," 10/847,781 and "Use of Nanoparticles to Adjust Refractive Index of Dental Compositions", 10/847,803 all three of which were filed on May 17, 2004.

Non-reinforcing fillers may be used such as quartz, cristobalite, calcium silicate, diatomaceous earth, zirconium silicate, montmorillonite such as bentonite, zeolite, including moleculer sieves such as sodium aluminium silicate, metal oxide powder such as aluminium or zinc oxide or their mixed oxides, barium sulphate, calcium carbonate, plaster, glass and plastic powder.

Suitable fillers are also reinforcing fillers such as e.g. pyrogenic or precipitated silicic acid and silica aluminium mixed oxides. The above-mentioned fillers can be hydrophobized, for example by treatment with organosilanes or siloxanes or by the etherification of hydroxyl groups to alkoxy groups. One type of filler or a mixture of at least two fillers can be used.

A combination of reinforcing and non-reinforcing fillers is particularly preferred. In this respect, the quantity of reinforcing fillers ranges from about 1 to about 10 wt.-%, in particular from about 2 to about 5 wt.-% of the curable composition. The difference in the named overall ranges, i.e. about 2 to about 89 wt.-% is accounted for non-reinforcing fillers.

Pyrogenically-prepared highly-disperse silicic acids which have preferably been hydrophobized by surface treatment are preferred as reinforcing fillers. The surface treatment can be carried out, for example with dimethyldichlorosilane, hexamethyldisilazane, tetramethylcyclotetrasiloxane or polymethylsiloxane.

Particularly preferred non-reinforcing fillers are quartzes, cristobalites, calcium carbonate and sodium aluminium silicates which can be surface-treated. The surface treatment can generally be carried out with the same methods as described in the case of the strengthening fillers.

Optional additive components like stabilizers, modifiers, dyes, pigments, thixotropic agents, flow improvers, thinning agents, polymeric thickeners, surfactant and diluting agent(s) can be added alone or in admixture.

The above described carbosilane compounds can be used as monomers a dental composition that are curable preferably via a cationic ring opening polymerization of epoxy groups.

The dental composition of the present invention can be used, for example, to prepare a dental filling material, crown and bridge material, veneer material, inlay or onlay, pit and fissure sealant or bonding material.

The dental compositions of the invention can be provided as a one-part mixture or as a multiple part mixture. This usually depends on the initiator used. If the initiator is a light cure initiator, the dental composition can be provided as a one-part mixture, if the initiator is a redox cure initiator, the dental composition should be provided as a multiple part mixture.

Therefore, the present invention also relates to a kit of parts, comprising a base part (i) and a catalyst part (ii), wherein the base part (i) comprises one or more carbosilane component and filler, and the catalyst part (ii) comprises initiator, and wherein the optional additive components may be present either in the base part or the catalyst part or in both parts.

The dental compositions of the invention is usually packaged in a container or cartridge, preferably in a dental compule. Examples of such compules are described in U.S. Pat. No. 5,322,440 A1 or 4,391,590 or 5,165,890.

The present invention also relates to a method of producing a curable dental composition comprising the steps a) providing carbosilane compound, initiator, optionally filler and optionally additive components;
b) mixing the components of step a),
wherein the carbosilan compound can be obtained via a hydrosilylation reaction comprising reacting
  a poly Si—H functional carbosilane component (aa) and
  an olefinic substituted aliphatic epoxy moiety containing component (bb)
or
wherein the carbosilan compound can be obtained via an epoxidation reaction comprising reacting
  an aliphatic olefinic precursor (dd) and
  an organic peracid (ee).

Preferably, the carbosilane compound of the invention can be synthesized via a hydrosilylation reaction (e.g. such as that described in Marciniec, B., Comprehensive Handbook on Hydrosilylation, Pergamon Press, Oxford, 1992) or via an epoxidation reaction (e.g. such as that described in Houben-Weyl, Methoden der Organischen Chemie, volume VI/3, p 385ff., Georg Thieme Verlag, Stuttgart, 1965, 4. edition).

The hydrosilylation reaction is an addition reaction where a SiH functional compound (aa) is added to an olefinic functional compound (bb) in the presence of a catalyst as indicated in scheme 1 forming a new Si—C single bond and yielding a silicon containing compound (cc):

scheme 1

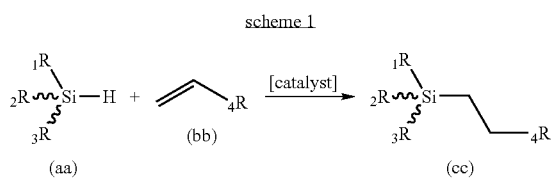

wherein $R_1$, $R_2$, $R_3$, $R_4$ may be selected independently of one another and represent aliphatic, cycloaliphatic, aromatic, (cyclo)aliphatic aromatic or aromatic (cyclo)aliphatic moieties wherein one or more C and H atoms can be replaced by substitutents which do not interfere with the hydrosilation reaction or cure of the carbosilane compound, e.g. O, Br, Cl, and Si atoms, and can contain functionalities like epoxy groups wherein at least one of $R_1$, $R_2$, $R_3$ represents an aromatic moiety with an aromatic ring bonded to the Si atom.

That is, the carbosilane compound of the present invention can be obtained via a hydrosilylation reaction according to scheme 1 by reacting a poly SiH functional carbosilane component (aa) with an olefinic substituted aliphatic epoxy moiety containing component (bb) using, for example, common noble metal compounds as catalysts as described, for example, for similar siloxane-based compounds in WO 98/22521 (see, for example, preparation examples 2-3 on pages 19-20).

Poly SiH functional carbosilane components (aa) such as 1,3,5-tris(dimethylsilyl)benzene and 2,4,6-tris(dimethylsilyl)anisole can be synthesized via an in situ Grignard reaction described, for example, in Beck, H., N., Chaffee, R., G., J. Chem. Eng. Data 1963, 8(3), 453-454.

Olefinic substituted aliphatic epoxy moiety containing components (bb) such as 1,2-epoxy-5-hexene, 1,2-epoxy-7-octene, and 1,2-epoxy-9-decene are commercially available.

Other precursors can also be used to make the carbosilane compound via an epoxidation reaction (for example, as described in. Houben-Weyl, Methoden der Organischen Chemie, volume VI/3, p 385ff., Georg Thieme Verlag, Stuttgart, 1965, 4. edition) of an olefinic precursor).

The epoxidation reaction is an oxidation reaction transforming a carbon:carbon double bond of an olefinic precursor (dd) into a three membered cyclic ether (ff) by use of e.g. an organic peracid $R_6$—$CO_3H$ (ee) as indicated in scheme 2:

scheme 2

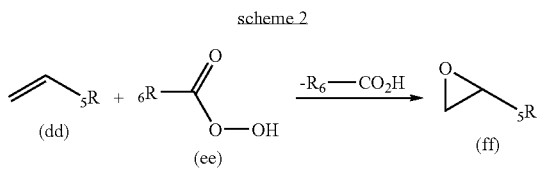

wherein $R_5$ represents an aliphatic, cycloaliphatic, aromatic (cyclo)aliphatic aromatic or aromatic (cyclo)aliphatic moiety, wherein one or more C or H atoms can be replaced by O, Br, Cl, and Si atoms and $R_6$ represents an aliphatic or aromatic moiety wherein one or more C or H atoms can be replaced by Br, Cl, F atoms.

That is, the carbosilane compound of the present invention can be obtained via an epoxidation reaction according to scheme 2 by reacting an aliphatic olefinic precursor (dd) with an organic peracid (ee) as described, for example, for similar siloxane based compounds in U.S. Pat. No. 4,788,268 (preparation examples 1, 2, 4, 5, 6, and 7 in columns 6-17).

Preferred aliphatic olefinic precursors (dd) like bis[4-allylphenyl]-dimethylsilane can be synthesized via a Grignard reaction as described, for example, for similar siloxane-based compounds in U.S. Pat. No. 4,788,268 (preparation examples 1, 2, 4, 5, 6, and 7 in columns 6-17) or via an in situ Grignard reaction as e.g. described for other carbosilane compounds by Beck, H., N., Chaffee, R., G., J. Chem. Eng. Data 1963, 8(3), 453-454.

The following compounds are examples of preferred poly SiH functional carbosilane components (aa) used according to scheme 1 for the synthesis of carbosilane compound fulfilling the requirements according to formula (Ia): Diphenyl-silane, Benzyl-phenyl-silane, (2-Phenylethyl)-phenyl-silane, Methyl-phenyl-silane.

The following compounds are examples of preferred olefinic substituted aliphatic epoxy moiety containing components (bb) used according to scheme 1 for the synthesis of carbosilane compound fulfilling the requirements according to formulas (Ia), (Ib), (II), (IIIa), (IV), (IVa) and (IVb):

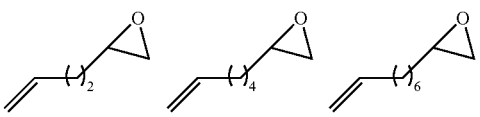

The following compounds are examples of preferred poly SiH functional carbosilane components (aa) which can be used according to scheme 1 for the synthesis of carbosilane compound fulfilling the requirements according to formula (Ib):

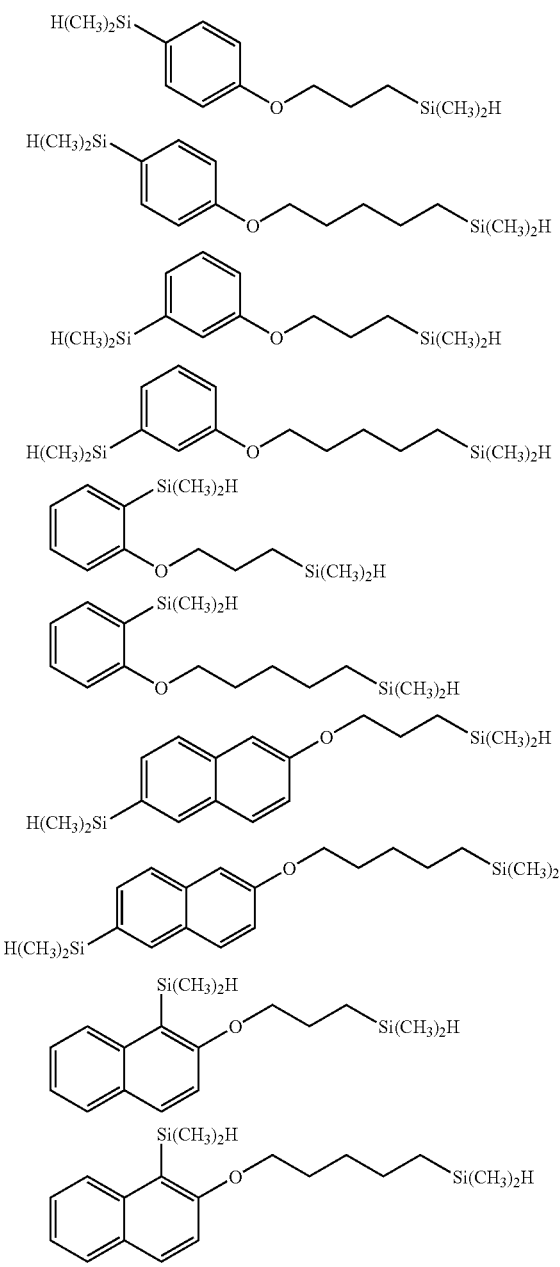

The following compounds are examples of preferred poly SiH functional carbosilane components (aa) used according to scheme 1 for the synthesis of carbosilane compound fulfilling the requirements according to formula (II):

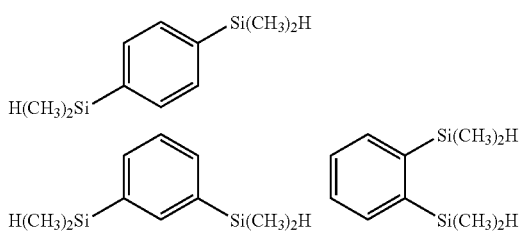

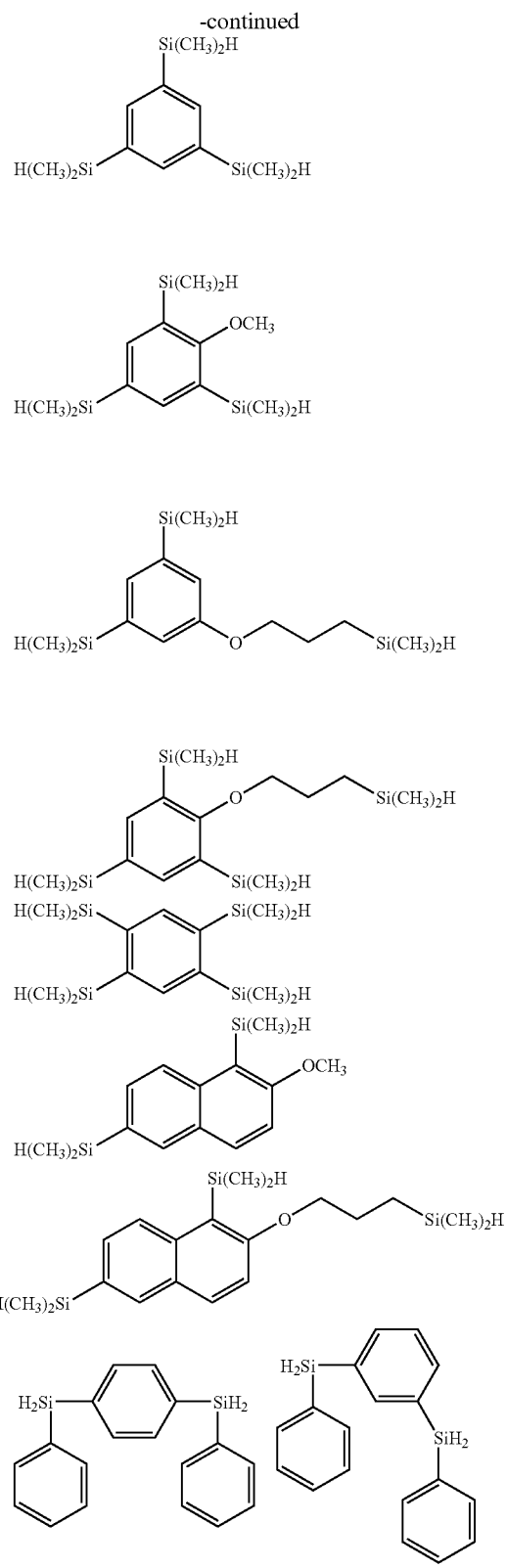

The following compounds are examples of preferred poly SiH functional carbosilane components (aa) used according to scheme 1 for the synthesis of carbosilane compound fulfilling the requirements according to formula (IIIa):

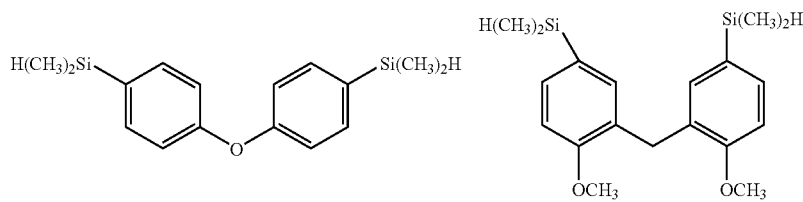
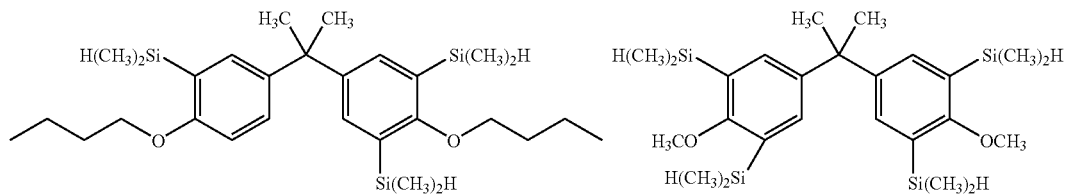
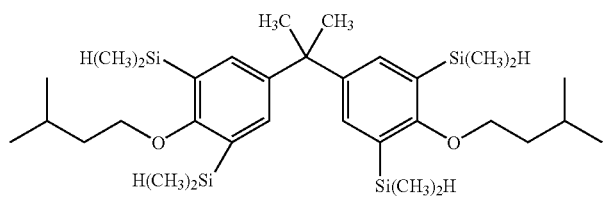
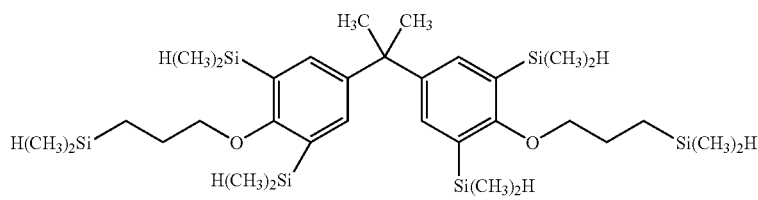
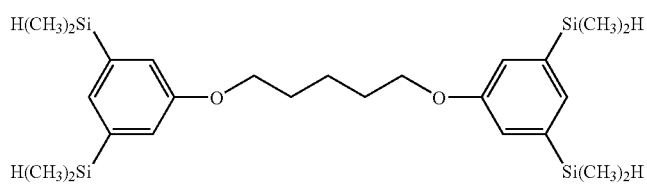
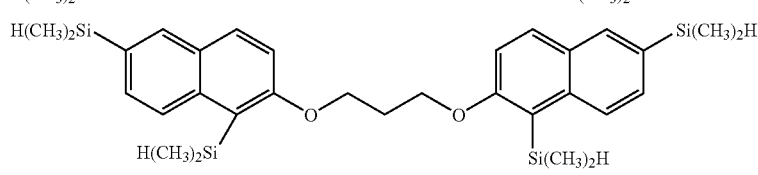

The following compounds are examples of preferred aliphatic olefinic precursors (dd) used according to scheme 2 for the synthesis of carbosilane compound fulfilling the requirements according to formula (IIIb):

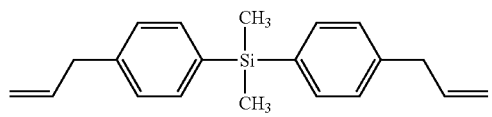

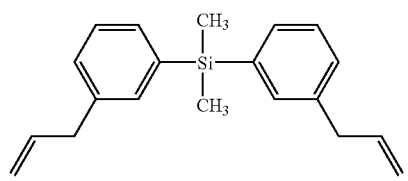

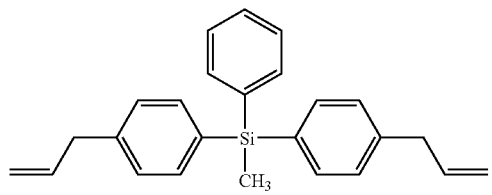

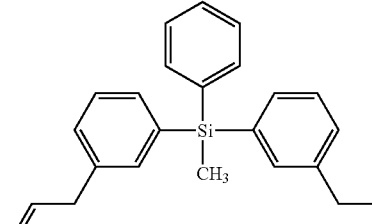

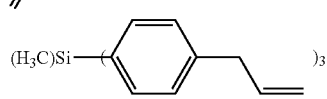

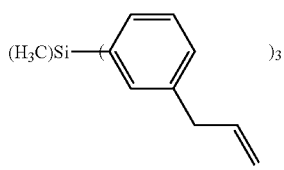

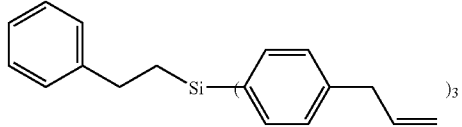

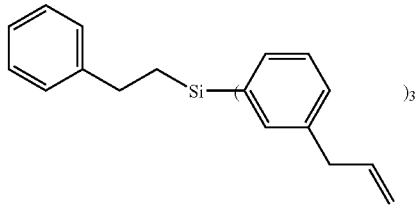

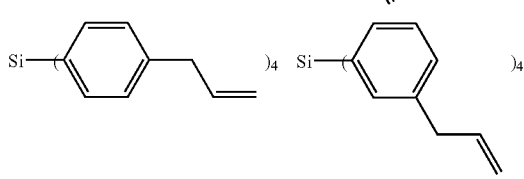

The following compounds are examples of preferred poly SiH functional carbosilane components (aa) used according to scheme 1 for the synthesis of carbosilane compound fulfilling the requirements according to formula (IV):

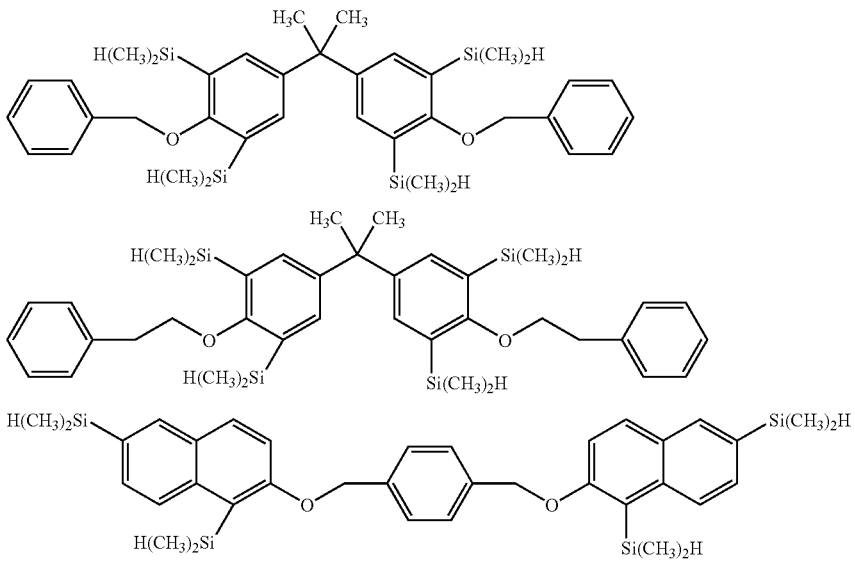

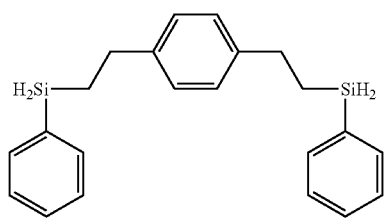
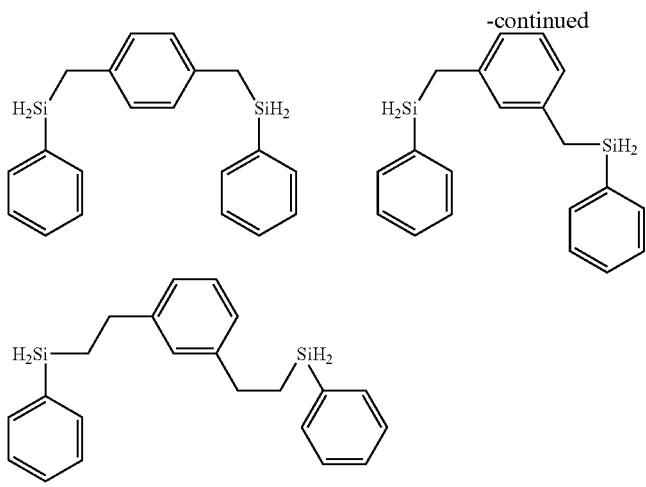
The following compounds are examples of preferred poly SiH functional carbosilane components (aa) used according to scheme 1 for the synthesis of carbosilane compound fulfilling the requirements according to formulas (IVa and IVb):
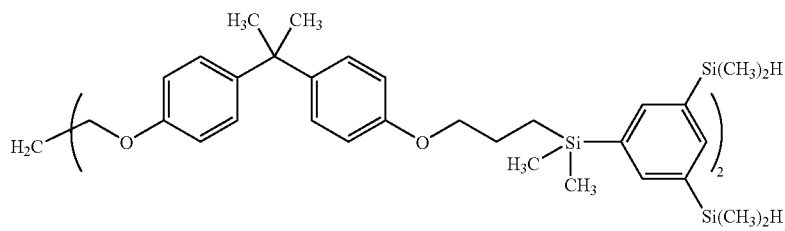
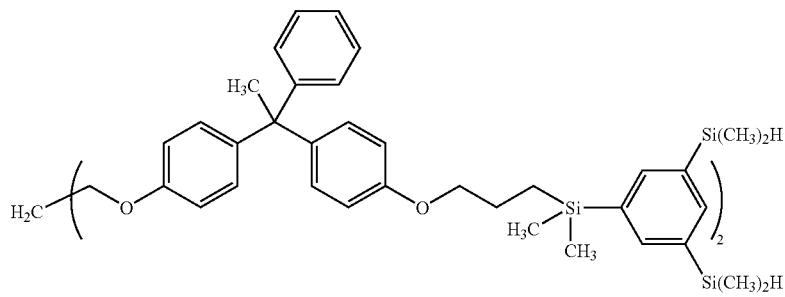
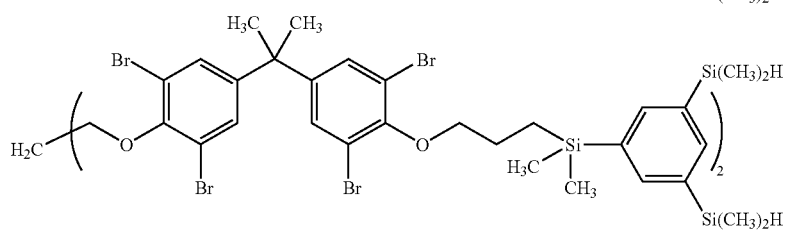
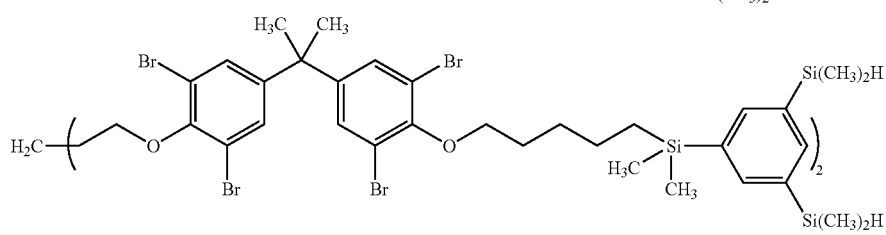

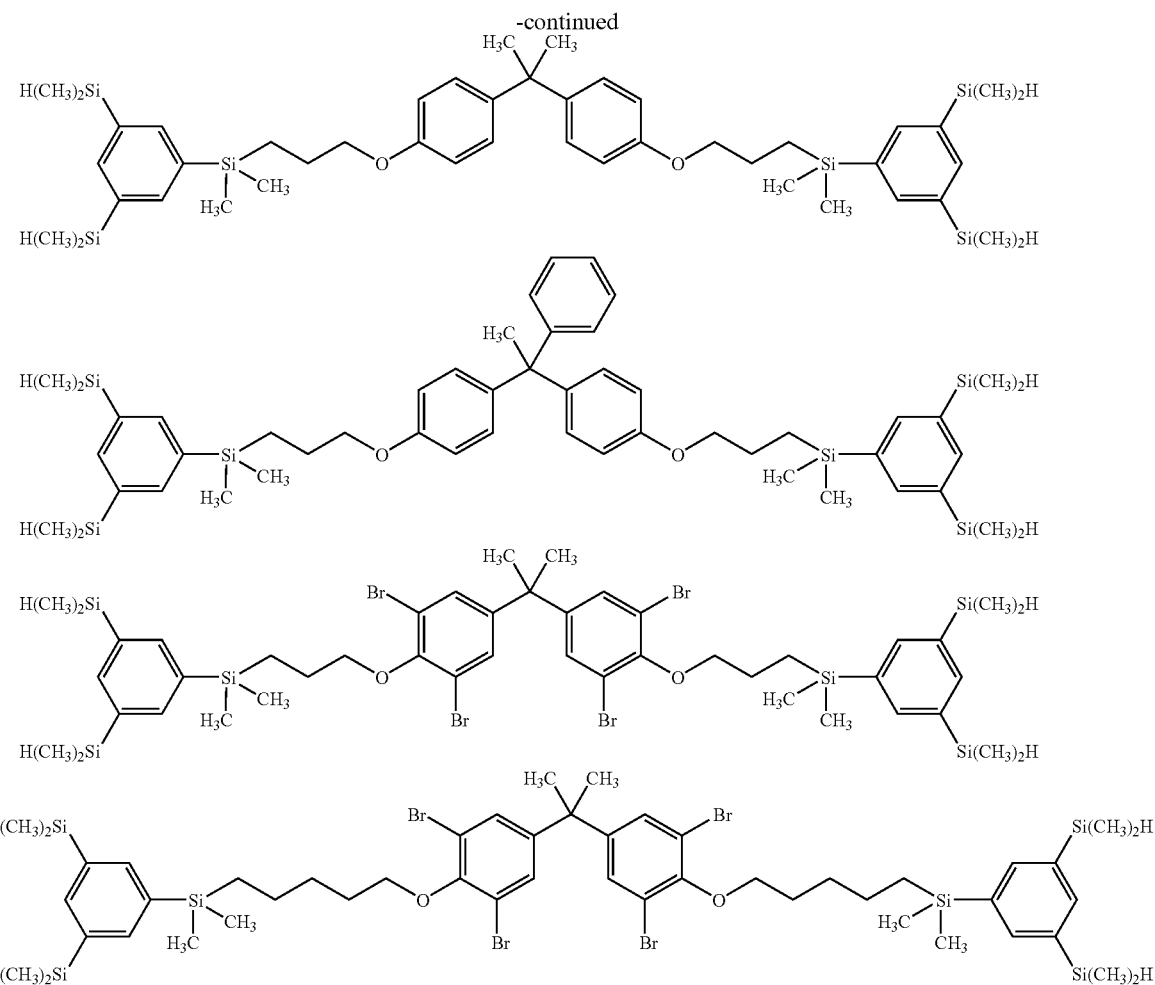
These poly SiH functional carbosilane components (aa) can be synthesized e.g. via a hydrosilylation reaction of a non silicon containing diolefinic precursor (bbb) and a poly SiH functional carbosilane component (aaa) used according to scheme 1 for the synthesis of a SiH compound (aa).
Preferred examples of non silicon containing diolefinic precursors (bbb) are:
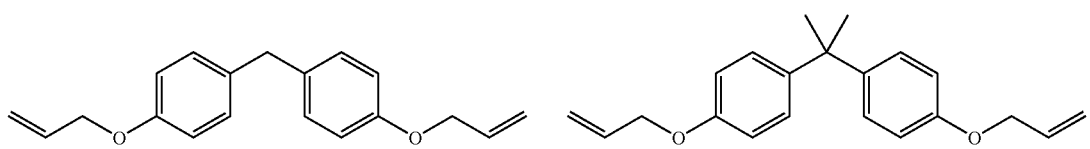
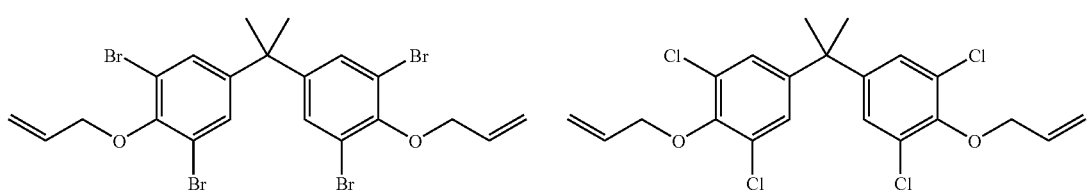

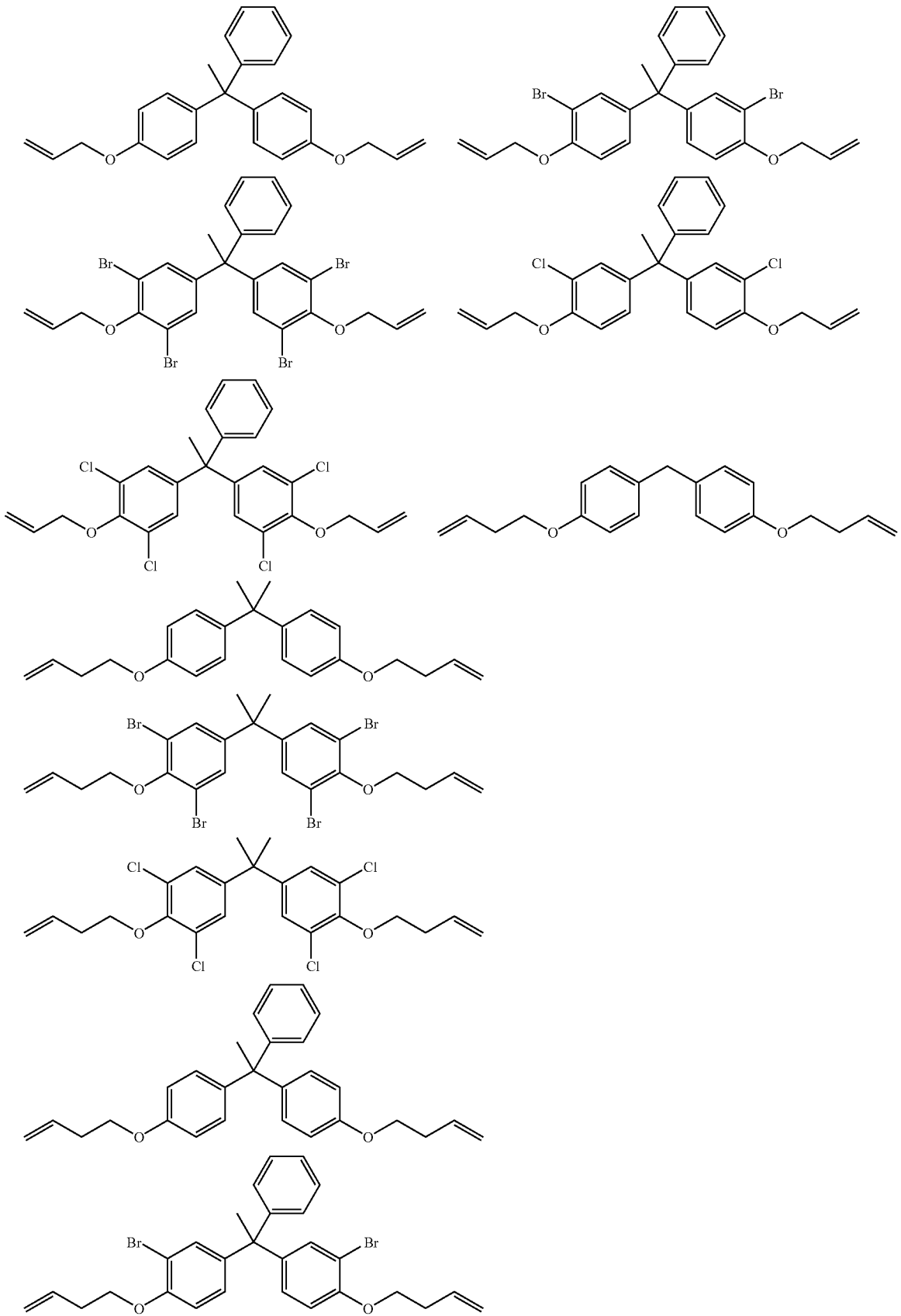

-continued
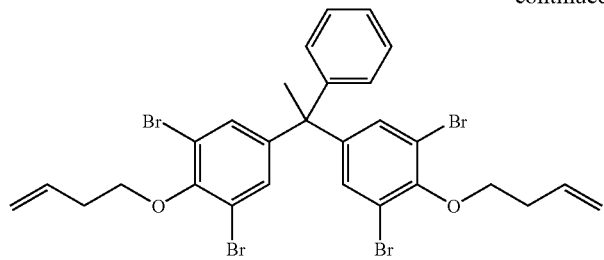
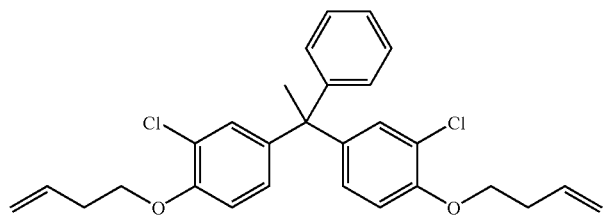
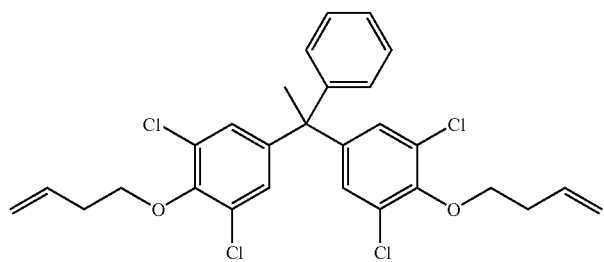
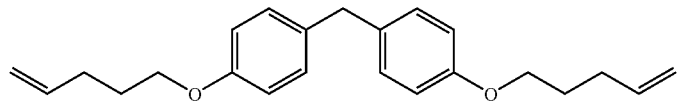
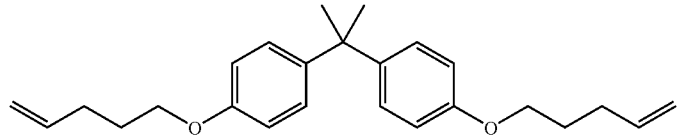
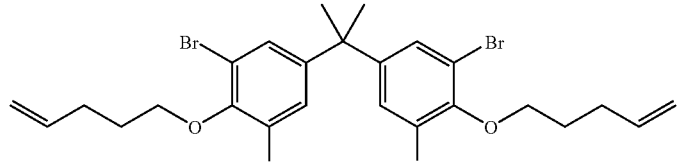
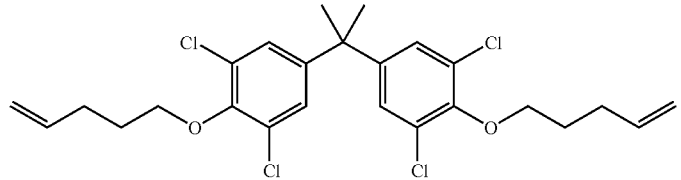
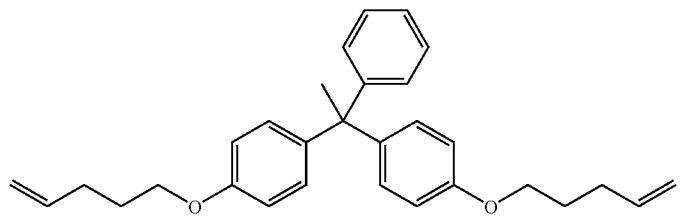

-continued
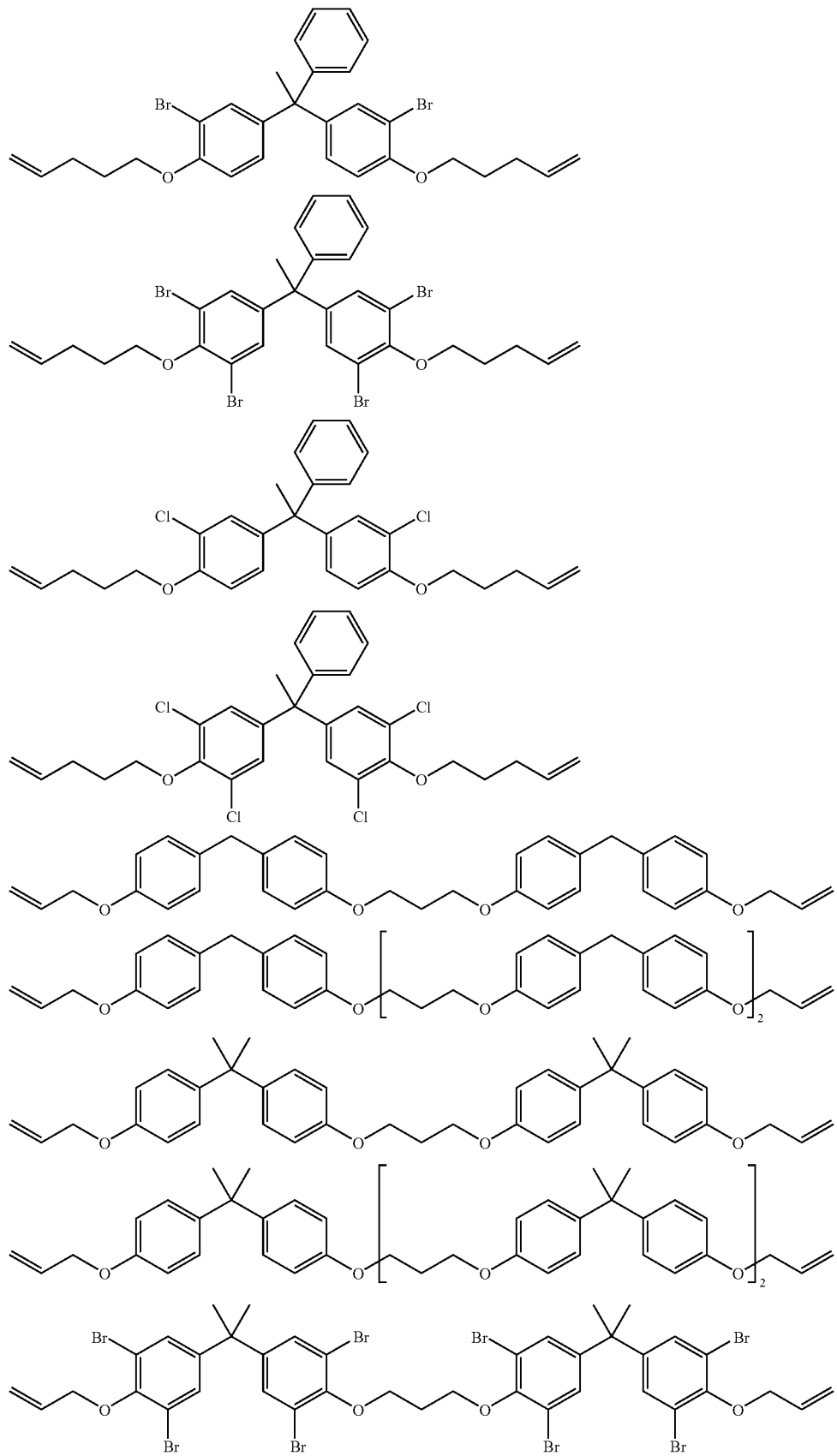

-continued
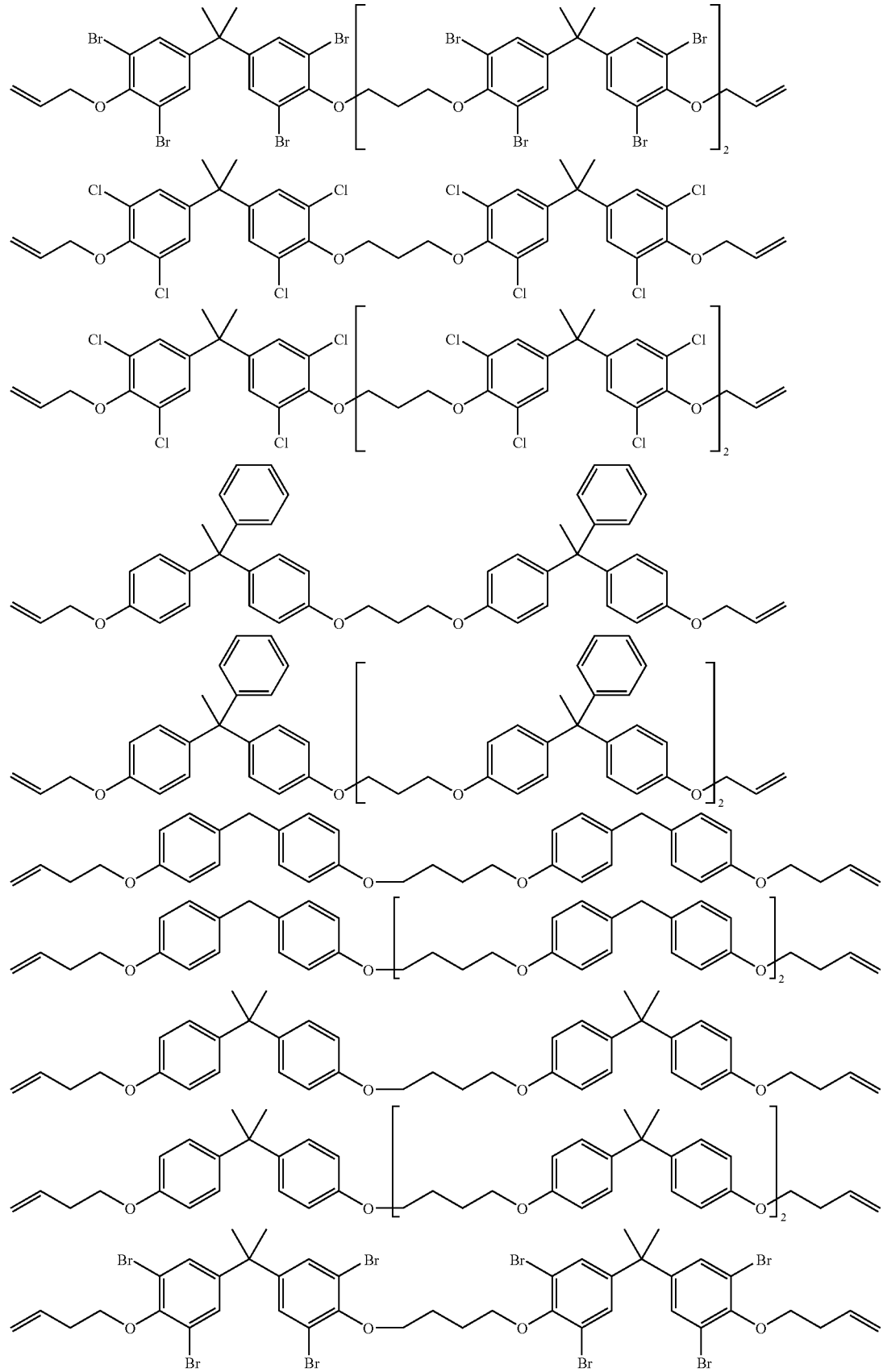

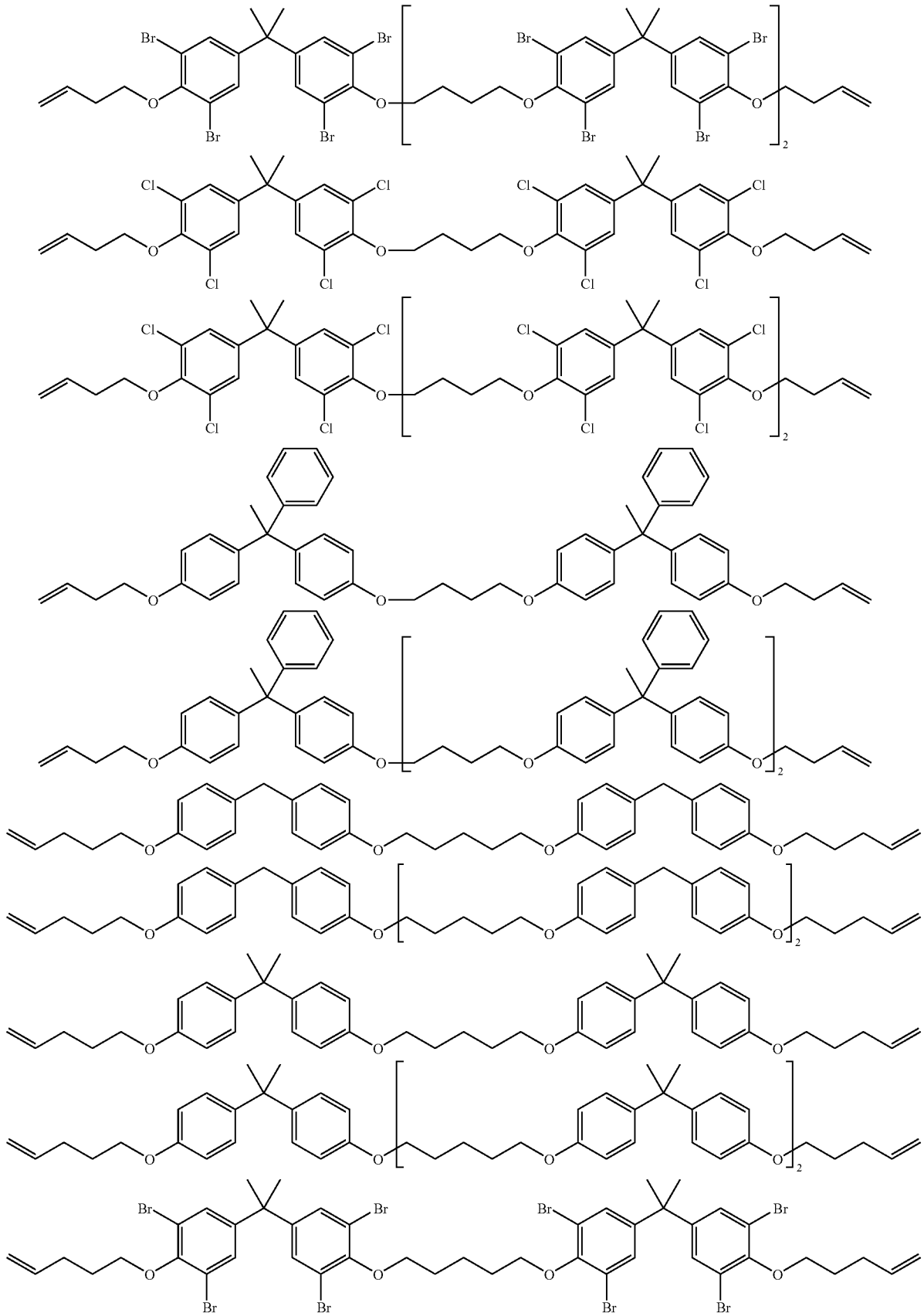

-continued

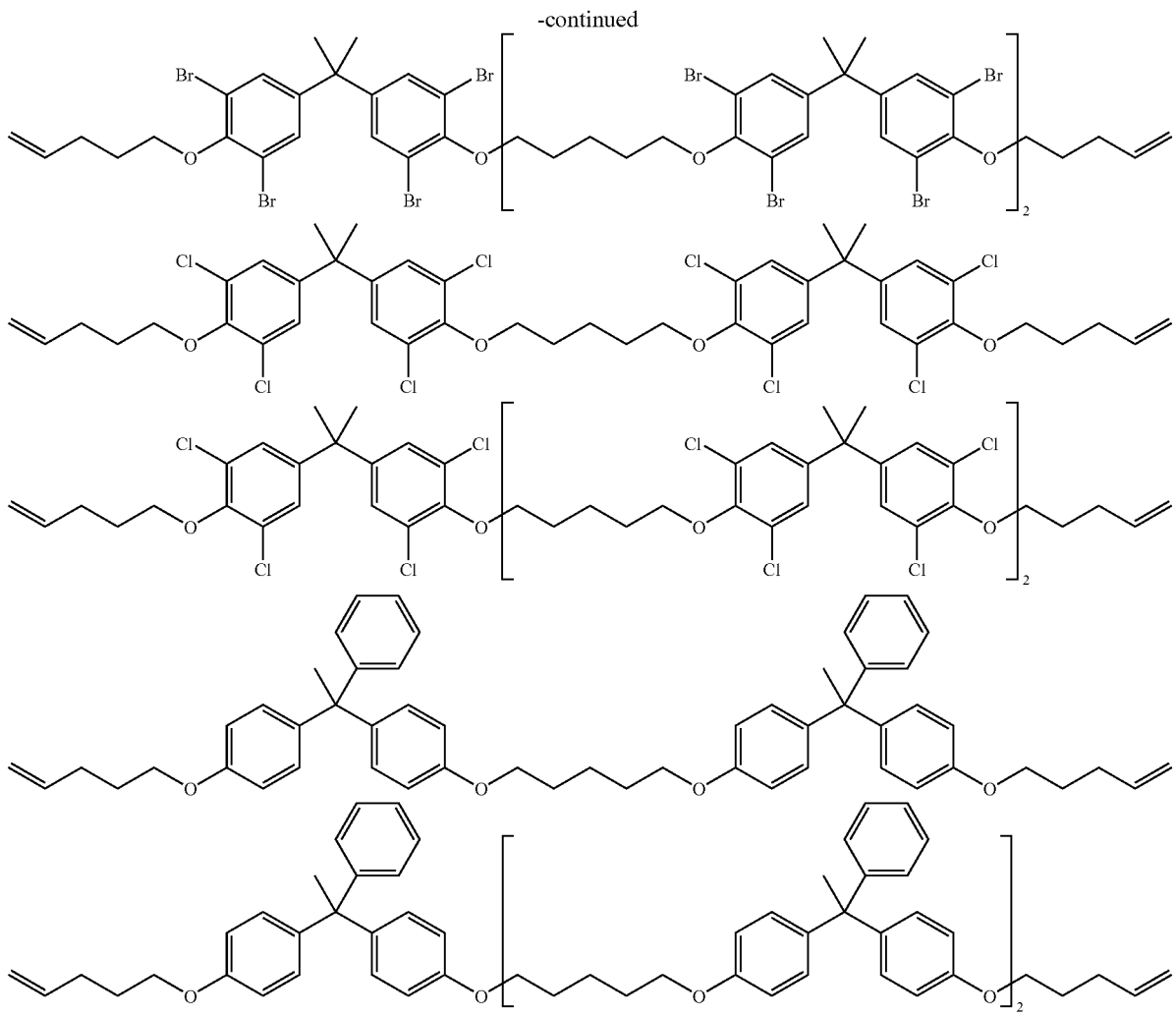

Preferred examples of poly SiH functional carbosilane components (aaa) are:

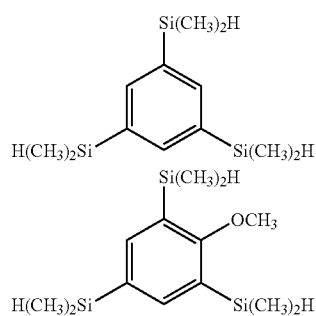

EXAMPLES

If not indicated otherwise, the measurements were done at standard temperature and pressure ("STP", i.e. 23° C. and 1023 hPa) according to the methods described below.

The refractive index of the carbosilane compound was measured with a Kruess AR 4 D device (refractometer according to Abbe's measure principle). The refractive index was measured at 20.0° C. The refractive index was measured at a wavelength of 589 nm.

The viscosity of the carbosilane compound was measured with a Haake RotoVisco RV1 device (rotor C60/1 for viscosities up to 8000 mPas or rotor C20/1 for viscosities above 8000 mPas together with stator P61). The viscosity was measured at 23.0° C. between two plane and parallel plates (i.e. stator and rotor). After activation and rectification of the system, the appropriate rotor was installed. Then the rotor was lowered and the distance between stator and rotor was adjusted to 0.052 mm (using Software RheoWin Pro Job Manager Software Version 2.94) for the viscosity measurement. Then the rotor was lifted and the material to be measured was given onto the stator (1.0 ml with rotor C60/1 or 0.04 ml with rotor C20/1). Without undue delay, the rotor was lowered into the preliminary adjusted measuring position. The material to be measured was tempered at 23.0° C. The shear rate for the measurement has to be adjusted to a value that the torque was at least 5000 μNm (therefore normally shear rates of 100, 200, 500, or 1000 $s^{-1}$ are used depending on the viscosity of the material to be measured). The measurement was started and run for 60 s. The viscosity values (Pas) were recorded starting 20 s after the start of measurement and the mean value of the recorded values was given as viscosity.

The molecular mass ($M_w$) of the carbosilane compound was determined with GPC.

The opacity of the cured dental composition was measured by means of specimens with a defined height of 3.6 (+/−0.1) mm and a diameter of 20 (+/−0.1) mm. These were prepared by filling the material to be checked into suitably high rings, evenly and free of bubbles, and illuminating it in overlapping areas and in the contact every 40 s by means of a lighting device (Trilight®, 3M ESPE) between plane, transparent, silicone oil treated glass slides. Then the opacity was measured with the colour measuring device "HunterLab LabScan Spectralcolorimeter" of Hunter Lab Associates Laboratory, Inc., USA (Software SpecWare Software Version 1.01) and given by the device in %-values.

The compressive strength and the flexural strength were measured comparably to ISO 9917 respectively according to ISO 4049. For the measurement of the compressive strength 10 specimens (3×3×5 mm) of each material were prepared according to the manufacturer's recommendations and the measurements were carried out comparably to ISO 9917 using an universal testing machine (Zwick Z 010, crosshead speed 4 mm/min).

The compressive strength is given in MPa. The measurement of the flexural strength was carried out according to ISO 4049 using an universal testing machine (Zwick Z 010, crosshead speed 2 mm/min). The flexural strength is given in MPa.

Examples

The invention is hereinafter described by examples. The examples are for illustrative purpose only and not intended to limit the invention.

The compounds listed in table 1 were prepared according to the references listed above and their refractive indices and viscosities were measured. For reference examples compounds known from the art were used. The examples 1 to 7 show the data for different carbosilane compound according to the present invention.

With the different carbosilane compound of table 1 and/or the compounds known from the art dental compositions according to table 2 were prepared and the opacity of the cured dental compositions was measured.

TABLE 1

| Examples of Compounds | Refractive Index | Viscosity [mPas] | Molecular mass [g/mol] |
|---|---|---|---|
| Reference Compound 1: 1,3,5,7-Tetrakis[2-(3,4-epoxycyclohexyl)-ethyl]-1,3,5,7-tetramethyl-cyclotetrasiloxane | 1.496 | 3100 | 736.2 |
| Reference Compound 2: 1,3,5-Tris[2-(3,4-epoxycyclohexyl)-ethyl]-7-(5,6-epoxyhexyl)-1,3,5,7-tetramethyl-cyclotetrasiloxane | 1.488 | 1200 | 710.2 |
| Example 1: 1,4-Bis[dimethyl-(5,6-epoxyhexyl)-silyl]-benzene | 1.510 | 200 | 386.7 |
| Example 2: 1,3,5-Tris[dimethyl-(5,6-epoxyhexyl)-silyl]-benzene | 1.505 | 400 | 547.0 |
| Example 3: 4,4'-Bis[dimethyl-(5,6-epoxyhexyl)-silyl]-diphenyl-ether | 1.539 | 300 | 482.8 |
| Example 4: Bis[4-(2,3-epoxypropyl)-phenyl]-dimethyl-silane | 1.561 | 300 | 324.5 |
| Example 5: Bis[4-(2,3-epoxypropyl)-phenyl]-methyl-phenyl-silane | 1.598 | 18600 | 386.6 |
| Example 6: Tris[4-(2,3-epoxypropyl)-phenyl]-methyl-silane | 1.594 | 42000 | 442.6 |
| Example 7: Bis(5,6-epoxyhexyl)-methylphenyl-silane | 1.513 | 30 | 318.5 |
| Example 8: Bis(5,6-epoxyhexyl)-diphenyl-silane | 1.552 | 200 | 380.6 |
| Example 9: 2,2-Bis{3,5-bis[dimethyl-(5,6-epoxyhexyl)-silyl]-4-methoxy-phenyl}-propane | 1.521 | 1400 | 881.5 |
| Example 10: 2,2-Bis{3,5-bis[dimethyl-(5,6-epoxyhexyl)-silyl]-4-(3-[dimethyl-(5,6-epoxyhexyl)-silyl]-propyloxy)-phenyl}-propane | 1.519 | 2900 | 1250 |

TABLE 2

| Amounts in % weight | examples of dental compositions | | | | | | | | | | | | |
|---|---|---|---|---|---|---|---|---|---|---|---|---|---|
| | 11 | 12 | 13 | 14 | 15 | 16 | 17 | 18 | 19 | 20 | 21 | 22 | 23 |
| Reference Compound 1 | 26.0 | | 12.4 | | 12.4 | 13.0 | 13.0 | 13.0 | 13.0 | 15.6 | 13.0 | | |
| Reference Compound 2 | | 26.0 | | | | | | | | | | | |
| Example 1 | | | 12.4 | | | | | | | | | | |
| Example 2 | | | | 24.7 | 12.4 | | | | | | | | |
| Example 3 | | | | | | 13.0 | | | | | | | |
| Example 4 | | | | | | | 13.0 | | | | | | |
| Example 5 | | | | | | | | | 13.0 | | | | |
| Example 6 | | | | | | | | | | 6.5 | | | |
| Example 7 | | | | | | | | 13.0 | | | | | |
| Example 8 | | | | | | | | | | 3.9 | 13.0 | | |
| Example 9 | | | | | | | | | | | | 26.0 | |
| Example 10 | | | | | | | | | | | | | 26.0 |
| Initiator sytem | I) | I) | I) | I) | I) | I) | I) | I) | I) | I) | I) | I) | I) |
| Filler | II a) | II a) | II b) | II b) | II b) | II a) | II a) | II a) | II a) | II a) | II a) | II a) | II a) |
| Opacity [%] | 97.7 | 97.2 | 90.3 | 84.2 | 92.2 | 83.7 | 86.3 | 80.7 | 84.9 | 80.2 | 76.9 | 79.4 | 81.7 |
| Exact Height of Specimen [mm] | (3.7) | (3.5) | (3.6) | (3.6) | (3.6) | (3.7) | (3.6) | (3.6) | (3.6) | (3.6) | (3.6) | (3.6) | (3.6) |

I) Initiator system: 0.8% (4-Tolyl)-(4-cumyl)-iodonium Tetrakis(pentafluorophenyl)borate, 0.1% Anthracene, 0.2% Camphorquinone II) Filler: a) 61.0% Silaned Quartz, mean particle size <2 µm, 11.9% $YF_3$, b) 62.9% Silaned Quartz, mean particle size <2 µm, 11.3% $YF_3$

The invention claimed is:

1. A curable dental composition comprising:
  a) at least one carbosilane compound comprising
    at least one Si-Aryl bond,
    at least one silicon atom,
    no Si-Oxygen bond, and
    at least one aliphatic epoxy moiety,
    wherein the carbosilane compound has no glycidyl ether moieties; and
  b) an initiator,
  wherein the carbosilane compound comprises at least one group of the following general formula (A'):

Aryl-[Si(A)$_a$(D-B)$_b$]$_n$     (A')

wherein
  each A independently represents an aliphatic or cycloaliphatic moiety having one to six carbon atoms, an aromatic moiety having six to 14 carbon atoms or an aliphatic aromatic or aromatic aliphatic moiety having 8 to 16 carbon atoms,
  each B independently represents an aliphatic epoxy moiety having two to six carbon atoms,
  each D independently represents an aliphatic or cycloaliphatic moiety having two to 10 carbon atoms, an aromatic or aromatic aliphatic moiety having six to 14 carbon atoms,
  wherein one or more C or H atoms can be replaced by 0, Br, Cl or Si,
  each Aryl independently represents a substituted or non substituted aromatic moiety having six to 14 carbon atoms,
  a is 0, 1 or 2,
  b is 1, 2 or 3,
  a+b is 3, and
  n is 1, 2, 3, 4, 5 or 6.

2. The dental composition of claim 1, further comprising a filler.

3. The dental composition of claim 2, further comprising an additive selected from the group of modifiers, stabilizers, dyes, pigments, thixotropic agents, flow improvers, polymeric thickeners, surfactants, odorous substances, diluting agents and flavorings.

4. The dental composition of claim 1, wherein
  the carbosilane compound has a refractive index above 1.500;
  the carbosilane compound has a viscosity below 40 Pas;
  the carbosilane compound has a weight an average molecular mass from 300 to 10 000 g/mol; or
  the opacity of the cured dental composition is below 93%.

5. The dental composition according to claim 3, comprising
  from about 1 to about 90 wt.-% of the carbosilane compound,
  from about 0.01 to about 25 wt.-% of the initiator,
  from about 0 to about 90 wt.-% of the filler, and
  from about 0 to about 25 wt.-% of the additive,
  with respect to the whole composition.

6. The dental composition of claim 1, wherein the carbosilane compound comprises at least one group of the following general formula (A"):

Aryl-[Si(A)$_a$(D-B)$_b$]$_n$     (A")

wherein
  each A independently represents methyl, phenyl or 2-phenylethyl,
  each B independently represents 2,3-Epoxypropyl,
  each D independently represents an aliphatic or cycloaliphatic moiety having four to 8 carbon atoms or an aromatic aliphatic moiety having seven carbon atoms, wherein one or more C or H atoms can be replaced by O, Br, Cl, and Si,
  each Aryl independently represents benzene, (2,3-epoxypropyl)benzene, naphthalene, alkoxybenzene, alkoxy naphthalene, bisphenol A ether or bisphenol F ether,
  a is 0, 1 or 2,
  b is 1, 2 or 3,
  a+b is 3, and
  n is 1, 2, 3, 4, 5 or 6.

7. The dental composition of claim 1, wherein the carbosilane compound is represented by the following formula (Ia):

{Aryl-[Si(A)$_a$(D-B)$_b$]$_n$}$_m$     (Ia)

wherein
  m is 1,
  n is 1,
  and the other indices are as defined in claim 1.

8. The dental composition of claim 1, wherein the carbosilane compound is represented by the following formula (1b):

B-D-E-{Aryl-[Si(A)$_a$(D-B)$_b$]$_n$}$_m$     (Ib)

wherein
  m is 1,
  n is 1,
  E represents an aliphatic or cycloaliphatic moiety having five to 11 carbon atoms wherein one or more C or H atoms can be replaced by 0, Br, Cl or Si, and the other indices are as defined in claim 1.

9. The dental composition of claim 1, wherein the carbosilane compound is represented by the following formula (II):

{Aryl-[Si(A)$_a$(D-B)$_b$]$_n$}$_m$     (II)

wherein
  m is 1
  n is 2, 3, 4, 5 or 6 and
  the other indices are as defined in claim 1.

10. The dental composition of claim 1, wherein the carbosilane compound is represented by the following formula (IIIa):

F-{Aryl-[Si(A)$_a$(D-B)$_b$]$_n$}$_m$     (IIIa)

wherein
  m is 2, 3 or 4
  n is 1, 2, 3, 4, 5 or 6,
  F represents an aliphatic or cycloaliphatic moiety having 0 to 25 carbon atoms or an aromatic moiety having 0 to 20 carbon atoms wherein one or more C or H atoms can be replaced by O, Br, Cl or Si and
  the other indices are as defined in claim 1.

11. The dental composition of claim 1, wherein the carbosilane compound is represented by the following formula (IIIb):

Aryl-[Si(A)$_a$(D-B)$_b$]$_n$     (IIIb)

wherein
  Aryl represents (2,3-epoxypropyl)benzene,
  each A independently represents an aliphatic or cycloaliphatic moiety having one to six carbon atoms or an aromatic or aliphatic aromatic moiety having six to 16 carbon atoms,
  each B independently represents a terminal C$_2$ based epoxy moiety,
  each D independently represents an aromatic aliphatic moiety having seven to 14 carbon atoms, a is 0, 1 or 2;
b is 1, 2 or 3;
n is 1, and
the other indices are as defined in claim 1.

12. The dental composition of claim 1, wherein the carbosilane compound is represented by the following formula (IV):

G-{Aryl-[Si(A)$_a$(D-B)$_b$]$_n$}$_m$  (IV)

wherein
G represents an aliphatic, cycloaliphatic, aromatic, (cyclo)aliphatic aromatic or aromatic (cyclo)aliphatic moiety having one to 200 carbon atoms wherein one or more C or H atoms can be replaced by O, Br, Cl, and Si,
m is 2, 3 or 4,
n is 1, 2, 3, 4, 5 or 6, and
the other indices are as defined in claim 1.

13. The dental composition of claim 1, wherein the carbosilane compound is represented by one of the following formulas (IVa) and (IVb):

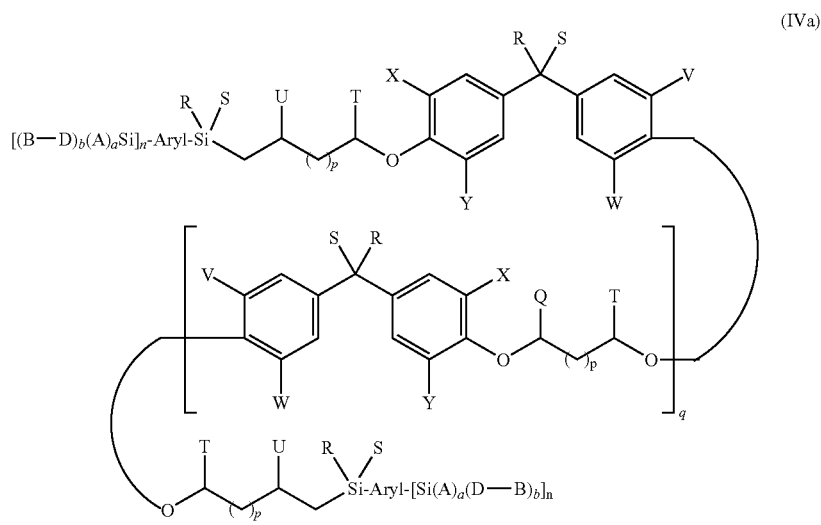

(IVa)

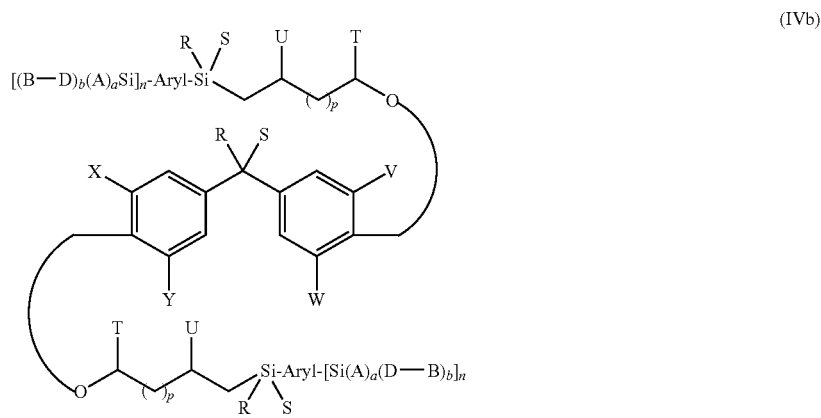

(IVb)

wherein
each Q independently represents H or methyl,
each R, S independently represent H, phenyl or a branched or unbranched alkyl moiety having one to 8 carbon atoms, wherein R and S together may form a cycloaliphatic ring,
each T, U independently represent H, methyl or ethyl, each V, W, X, Y independently represent H, Br, Cl or F, p is 0, 1, 2, 3 or 4 q is 0, 1, 2, 3, 4 or 5, and the other indices are as defined in claim 1.

14. The dental composition of claim 1, wherein the carbosilane compound is selected from the group consisting of

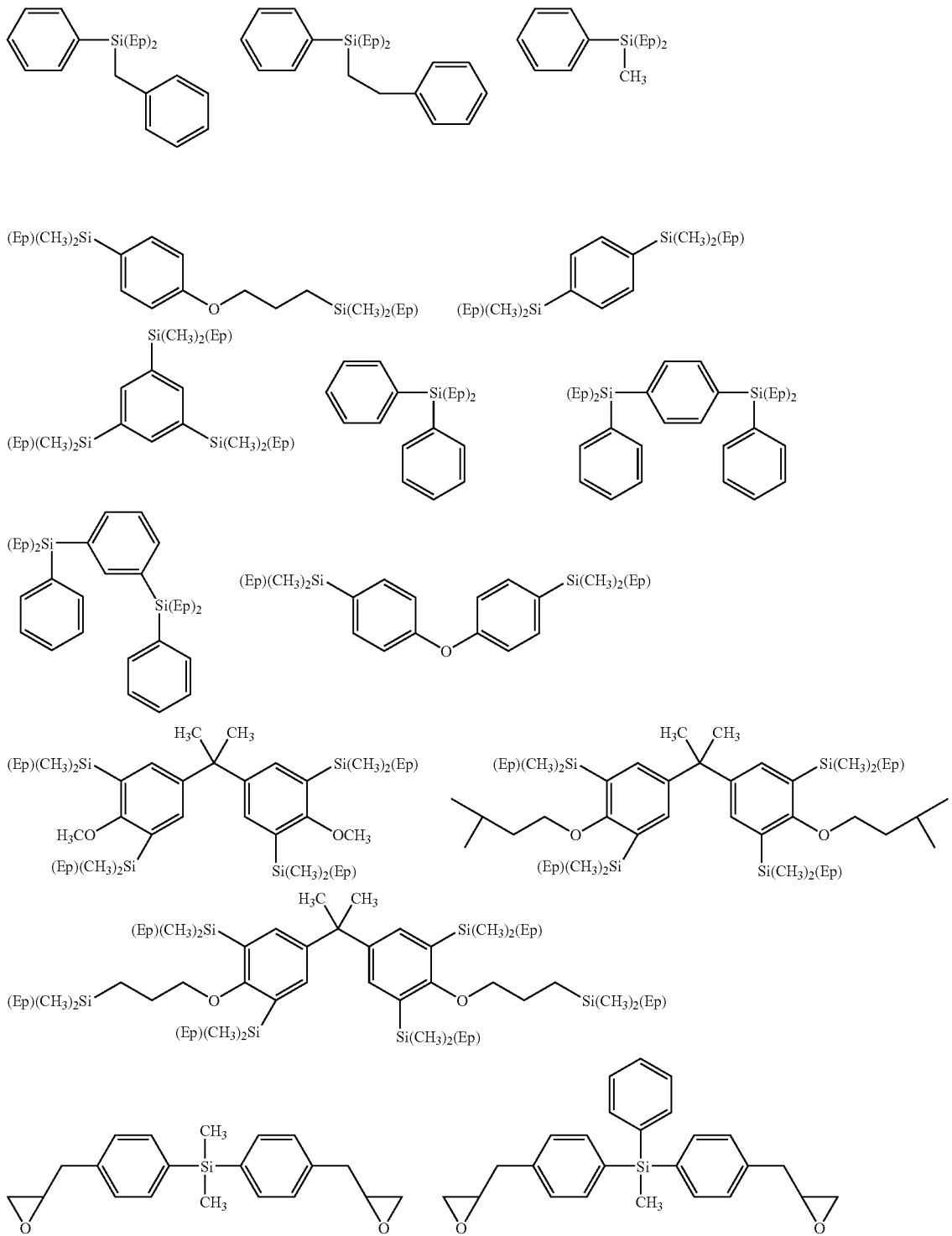

-continued
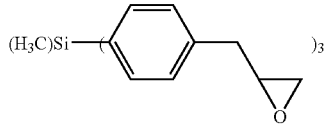
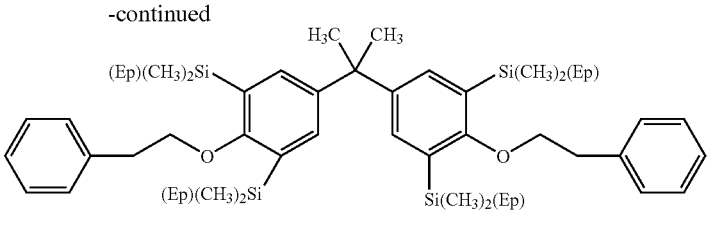
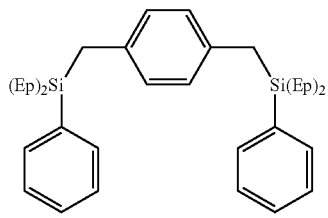
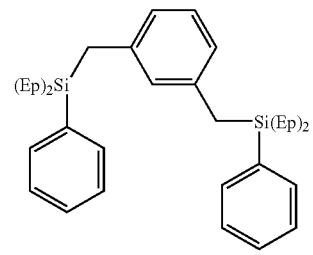
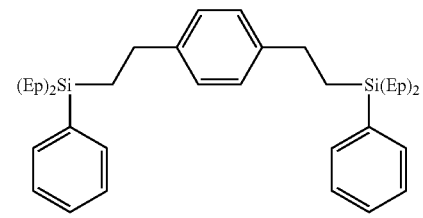
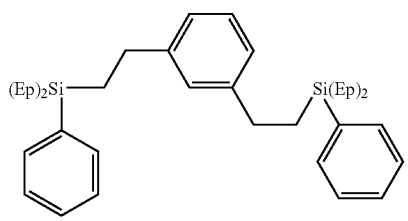
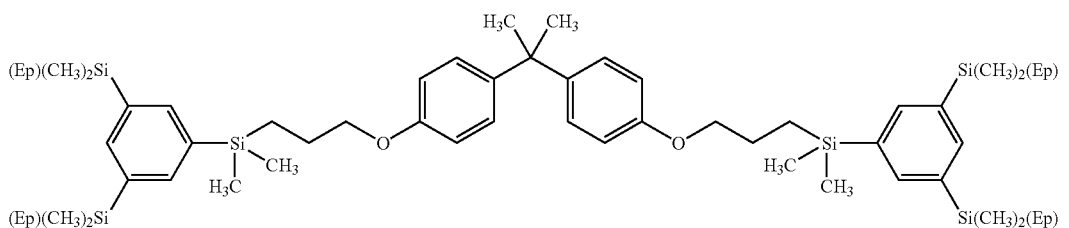
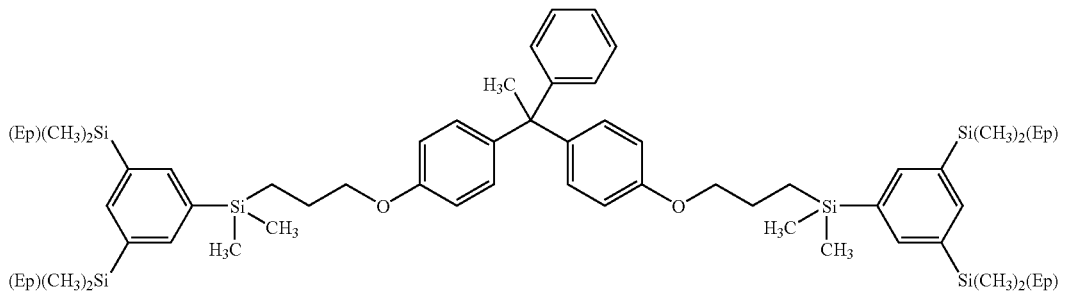
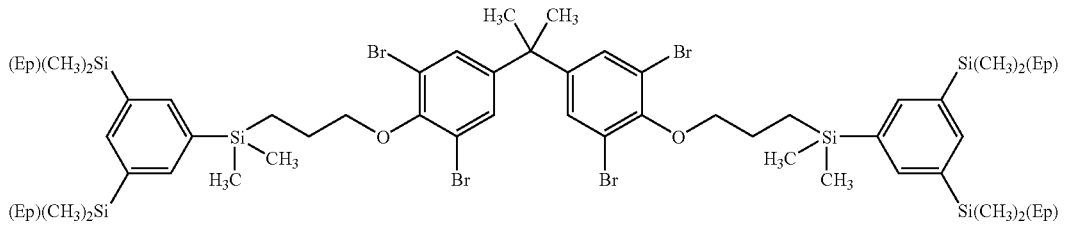

15. The dental composition of claim 1, wherein the initiator comprises a light curing initiator or a redox curing initiator or a combination of both.

16. The dental composition of claim 1, wherein the filler comprises reinforcing and/or non-reinforcing fillers.

17. A container or cartridge filled with the dental composition of claim 1.

18. A method for preparing a dental material comprising the steps of:

a) providing the dental composition of claim 1;
b) applying the dental composition to a surface; and
c) curing the dental composition.

19. The dental composition of claim 1, wherein at least one B comprises a terminal $C_2$ based epoxy moiety.

20. The dental composition of claim 6, wherein at least one D comprises an $\alpha,3$- or $\alpha,4$-toluenediyl with the phenyl ring attached to Si and the methylene group attached to aliphatic epoxy moiety B.

21. The dental composition of claim 11, wherein at least one D comprises an $\alpha,3$- or $\alpha,4$-toluenediyl.

* * * * *

UNITED STATES PATENT AND TRADEMARK OFFICE
CERTIFICATE OF CORRECTION

PATENT NO.        : 7,799,846 B2
APPLICATION NO.   : 11/572062
DATED             : September 21, 2010
INVENTOR(S)       : Adrian Eckert It is certified that error appears in the above-identified patent and that said Letters Patent is hereby corrected as shown below:

Column 10
Lines 60-65, delete

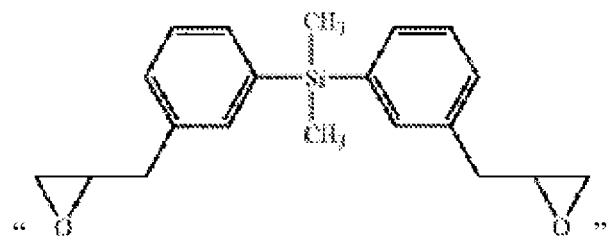

and insert in place thereof

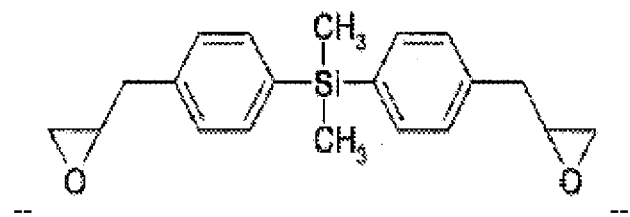

--.

Column 11
Line 11, delete

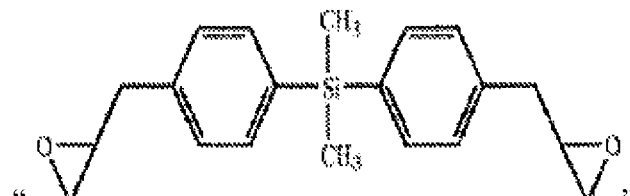

Signed and Sealed this
Third Day of July, 2012

David J. Kappos
*Director of the United States Patent and Trademark Office* and insert in place thereof

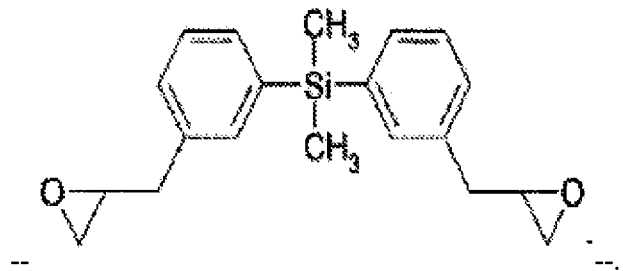

Column 19
Line 31, delete "iodoniumium" and insert in place thereof -- iodonium --.

Column 20
Line 9, delete "moleculer" and insert in place thereof -- molecular --.

Column 21
Line 4, delete "carbosilan" and insert in place thereof -- carbosilane --.
Line 10, delete "carbosilan" and insert in place thereof -- carbosilane --.
Line 42, delete "substitutents" and insert in place thereof -- Substituents --.

Column 45-46
Line 57, delete "sytem" and insert in place thereof -- system --.

Column 47
Line 27, in claim 1 delete "0" and insert in place thereof -- O --.

Column 48
Line 30, in claim 8 delete "0" and insert in place thereof -- O --.

Column 53-54
Line 5, in claim 14 after

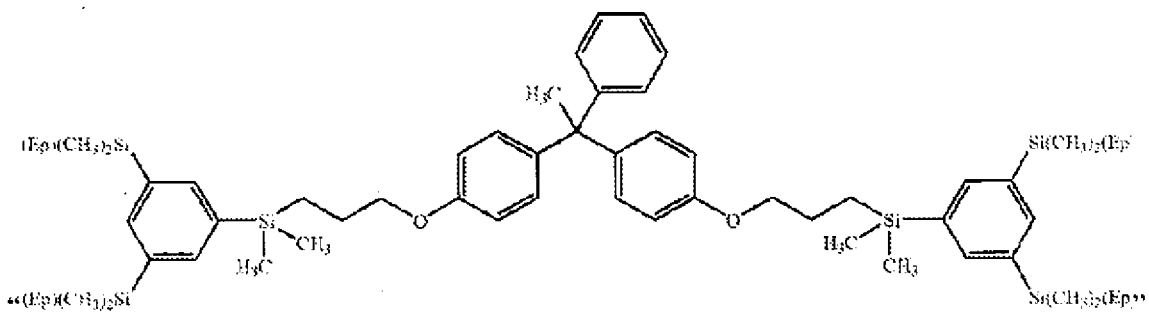

insert -- and --.

UNITED STATES PATENT AND TRADEMARK OFFICE
CERTIFICATE OF CORRECTION

PATENT NO.         : 7,799,846 B2
APPLICATION NO.    : 11/572062
DATED              : September 21, 2010
INVENTOR(S)        : Adrian Eckert It is certified that error appears in the above-identified patent and that said Letters Patent is hereby corrected as shown below:

Column 10
Lines 60-65, delete

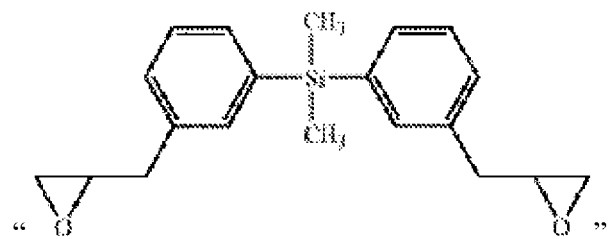

and insert in place thereof

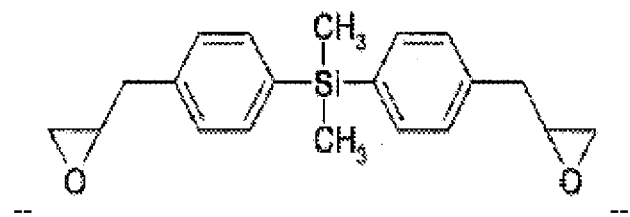

Column 11
Lines 1-8, delete

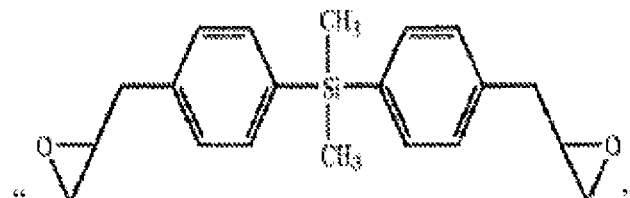

This certificate supersedes the Certificate of Correction issued July 3, 2012.

Signed and Sealed this
Fourteenth Day of August, 2012

David J. Kappos
Director of the United States Patent and Trademark Office and insert in place thereof

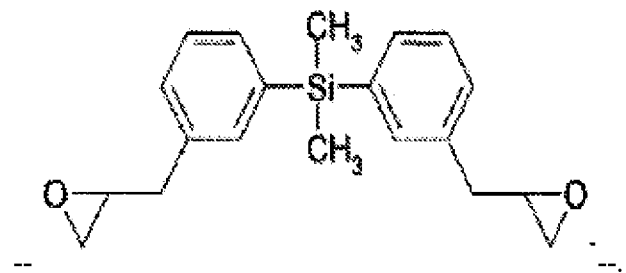

Column 19
Line 31, delete "iodoniumium" and insert in place thereof -- iodonium --.

Column 20
Line 9, delete "moleculer" and insert in place thereof -- molecular --.

Column 21
Line 4, delete "carbosilan" and insert in place thereof -- carbosilane --.
Line 10, delete "carbosilan" and insert in place thereof -- carbosilane --.
Line 42, delete "substitutents" and insert in place thereof -- Substituents --.

Column 45-46
Line 57, delete "sytem" and insert in place thereof -- system --.

Column 47
Line 27, in claim 1 delete "0" and insert in place thereof -- O --.

Column 48
Line 30, in claim 8 delete "0" and insert in place thereof -- O --.

Column 53-54
Line 5, in claim 14 after

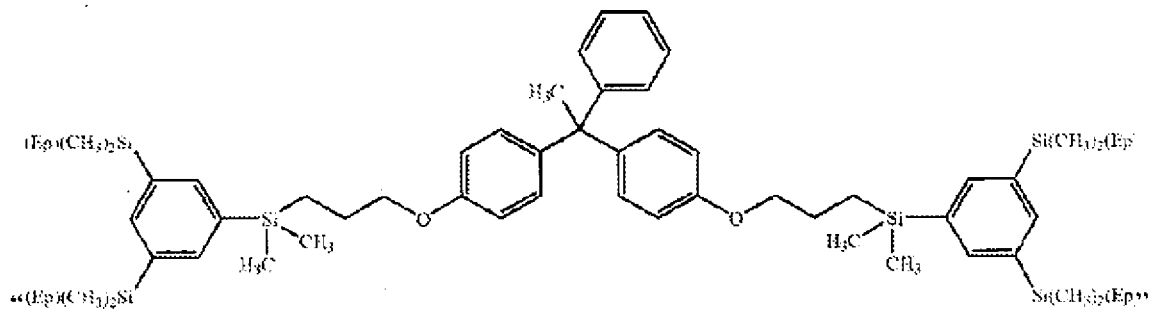

insert -- and --.